United States Patent
Esquivel-Upshaw et al.

(10) Patent No.: US 11,752,236 B2
(45) Date of Patent: Sep. 12, 2023

(54) METHODS AND COMPOSITIONS FOR MEDICAL IMPLANTS HAVING ANTI-BACTERIAL COATINGS

(71) Applicant: University of Florida Research Foundation, Inc., Gainesville, FL (US)

(72) Inventors: Josephine F. Esquivel-Upshaw, Gainesville, FL (US); Arthur E. Clark, Newberry, FL (US); Fan Ren, Gainesville, FL (US); Samira Afonso Camargo, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 17/759,760

(22) PCT Filed: Jan. 4, 2021

(86) PCT No.: PCT/US2021/012040
§ 371 (c)(1),
(2) Date: Jul. 29, 2022

(87) PCT Pub. No.: WO2021/154457
PCT Pub. Date: Aug. 5, 2021

(65) Prior Publication Data
US 2023/0066453 A1    Mar. 2, 2023

Related U.S. Application Data

(60) Provisional application No. 62/968,935, filed on Jan. 31, 2020.

(51) Int. Cl.
*A61L 27/30* (2006.01)
*A61L 27/04* (2006.01)
(Continued)

(52) U.S. Cl.
CPC ............. *A61L 27/306* (2013.01); *A61L 27/04* (2013.01); *A61L 27/10* (2013.01); *A61L 27/54* (2013.01);
(Continued)

(58) Field of Classification Search
CPC ........ A61L 27/54; A61L 27/10; A61L 27/306; A61K 6/58
See application file for complete search history.

(56) References Cited

U.S. PATENT DOCUMENTS

| 5,571,758 A | 11/1996 | Grossman |
| 2014/0277571 A1* | 9/2014 | Pettersson ............... A61L 27/10 |
| | | 204/192.15 |
| 2017/0165039 A1* | 6/2017 | Towse ...................... A61K 6/58 |

FOREIGN PATENT DOCUMENTS

WO    WP2008/096160    *    2/2008    ............. A61L 27/54

OTHER PUBLICATIONS

Carey et al., Antibacterial Properties of Charged TiN Surfaces for Dental Implant Applications, Aug. 2019, 4(31), pp. 9185-9189 (Year: 2019).*

(Continued)

*Primary Examiner* — Dah-Wei D. Yuan
*Assistant Examiner* — Andrew J Bowman
(74) *Attorney, Agent, or Firm* — THOMAS | HORSTEMEYER LLP

(57) ABSTRACT

In one aspect, the disclosure relates to protective, anti-bacterial coatings for medical implants and methods of making the same. Also disclosed herein are methods for improving the anti-bacterial properties of a medical device coated with silicon carbide (SiC) or titanium nitride (TiN). Further disclosed herein are medical devices including an anti-microbial layer prepared by the disclosed methods. This abstract is intended as a scanning tool for purposes of searching in the particular art and is not intended to be limiting of the present disclosure.

18 Claims, 24 Drawing Sheets

(51) Int. Cl.
    *A61L 27/10*       (2006.01)
    *A61L 27/54*       (2006.01)
    *A61L 31/08*       (2006.01)

(52) U.S. Cl.
    CPC ......... *A61L 31/08* (2013.01); *A61L 2300/404* (2013.01); *A61L 2430/12* (2013.01); *A61L 2430/24* (2013.01)

(56) References Cited

OTHER PUBLICATIONS

Carey et al 'Antibacterial Properties of Charged TiN Surfaces for Dental Implant Application' ChemistrySelect; 2019, 4:9185-9189.
Chen et al 'Demonstration of SiO2/SiC based protective coating for dental ceramic prostheses' Journal of the American Ceramic Society, 2019; 102:6591-6599.
Rodrigues et al 'Titanium Corrosion Mechanisms in the Oral Environment: A Retrieval Study' (13-17, 19)/(1-12), 18/9 Materials, 2013, 6:5258-5274.
Wikpedia 'Titanium Nitride' retrieved from <https://en.wikipedia.org/wiki/Titanium_nitride> accessed Jul. 28, 2022.
FDA.gov Temporomandibular Joint (TMJ) Implants Dec. 12, 2010 (Dec. 12, 2019) retrieved from <https://web.archive.org/web/20191212150255/https://www.fda.gov/medicaldevices/temporomandibular-disorders-tmd-devices/temporomandibular-joint-tmj-implants>.
International Search Report and Written Opinion for PCT/US2021/012040 dated Mar. 25, 2021; 18pp.

\* cited by examiner

METHODS AND COMPOSITIONS FOR MEDICAL IMPLANTS HAVING ANTI-BACTERIAL COATINGS

CROSS REFERENCE TO RELATED APPLICATIONS

This application is a U.S. national phase application under 35 U.S.C. 371 of International Patent Application No. PCT/US2021/012040, filed Jan. 4, 2021, which claims priority upon U.S. Provisional Application No. 62/968,935, filed on Jan. 31, 2020, both of which are incorporated herein by reference in their entirety.

STATEMENT REGARDING FEDERALLY SPONSORED RESEARCH OR DEVELOPMENT

This invention was made with government support under R01-DE025001 awarded by the National Institutes of Health. The government has certain rights in the invention

BACKGROUND

Approximately 5% of all dental implants anchored by osseointegration will fail within 10 years. Implant survival is not well characterized as a function of lifestyle; explorations into patients' past dental histories and other medical conditions have provided few predicating variables. Patients with previous history of periodontal disease have lower implant survival rates, but diseases such as osteoporosis or diabetes are not consistent predictors of implant failure.

A primary culprit for implant failure is peri-implantitis, or site-specific bacterial infection, which leads to bone loss around the implant as well as soft tissue inflammation. This definition assumes that there was successful initial osseointegration of the implant, and thus that the disease is degenerative, which excludes implant failure due to infection during the implantation procedure or mechanical failure of the implant. Peri-implantitis has no conclusive treatment to stop infection and progression of the disease, thus prevention of the disease at the earliest of stages is of utmost importance to extend implant lifetime. The infection site's bacterial flora have been explored to determine if a prevalence of certain species may increase incidence of peri-implantitis. The sub-gingival flora of sites with peri-implantitis have similar flora to those identified in cases of periodontitis, with the majority of bacteria being Gram negative. Nineteen bacterial species having higher counts at the site of peri-implantitis infection than at implant sites without infection have been identified, with 7 strains accounting for 30% of bacterial flora at the infection site, compared to 14% at non-infected implants. Furthermore, peri-implantitis can, in some instances, progress to pen-implant disease, which is characterized by mucosal inflammation surrounding an implant with or without 2 mm or more of bone loss after restoration.

Dental implants can be susceptible to peri-implantitis and peri-mucositis which are diseases of the supporting structures of the implant. Peri-implantitis is disease of the supporting structures of the implant, resulting in bone loss and tissue inflammation. The prevalence of peri-implantitis was shown to be as high as 85.0% and the incidence at 43.9% within 5 years. The most effective treatment for peri-implantitis is prevention by minimizing bacterial colonization and implementing implant maintenance regimens. Therefore, there is a critical need to develop preventive strategies, such as implant surface modification, to minimize bacterial colonization, proliferation, and surface corrosion of the implant.

Biofilms can be described as micro-ecosystems formed by various species of microorganisms, surrounded by a protein extracellular matrix and polysaccharides generated by the microorganisms. Oral biofilms are responsible for plaque formation leading to dental caries, periodontal disease, peri-implantitis, and enamel demineralization. Oral biofilms can adhere to both biotic and abiotic surfaces, such as prostheses, implants, and host tissues. Bacterial adhesion to substrates is a multifactorial process that involves surface properties inherent to both the bacteria and the substrate. Bacteria present in the oral cavity naturally tend to adhere to ceramic materials and also to the interface between tooth and prosthesis, implant, or the like. Typical adhesion is observed on the cervical third of the proximal surface of the prosthesis or implant and along the gingival margin where the biofilms are protected from mechanical action.

On solid surfaces such as enamel, the ability to aggregate, the order of appearance of the microorganisms, and the environment are essential factors in oral biofilm formation. The composition of the prosthesis or implant material as well as the surface structure can influence the initial bacterial adhesion and compromise dental health. Additionally, poor oral hygiene and/or a compromised immune system can be contributing factors that aid colonization. Bacteria that aggregate in biofilms release acidic compounds that can demineralize the hydroxyapatite in enamel as well as inducing inflammatory reactions in soft tissue and bone.

Since dental materials are in direct contact with the oral environment for long periods, biocompatibility of their component parts and materials is an important consideration. Studies have demonstrated that different glass-ceramics for prosthetic restorations, such as lithia-silica glass-ceramics, glass-zirconia materials, and feldspathic glass-ceramics all possess excellent biocompatibility.

The degradation of titanium (Ti) and the corresponding native surface oxide has been shown to result in the release of Ti ions into the surrounding tissue, which can initiate inflammatory reactions and often lead to peri-implantitis. Implants removed from a patient's oral cavity due to peri-implantitis often demonstrate pitting, a result of titanium corrosion. In vitro studies have observed Ti corrosion through scanning electron microscopy (SEM), energy dispersive spectroscopy (EDS), X-ray diffraction (XRD), X-ray photoelectron spectroscopy (XPS), and atomic force microscopy (AFM). Meanwhile, inductively coupled plasma mass spectrometry (ICP-MS) can measure Ti levels released in solution from corrosion processes.

Previous studies have demonstrated that oral bacteria not only contribute to titanium corrosion but can also expedite the process. *Porphyromonas gingivalis* (*P. gingivalis*), among other microorganisms, is present in high numbers during biofilm organization on titanium implants and have been shown to be a part of the characteristic bacterial profile in peri-implantitis. Oral bacteria such as *Actinomyces naeslundii* (*A. naeslundii*) and *Streptococcus mutans* (*S. mutans*) decrease the pH of their environment by generating organic acids, which break down the oxide layer and compromise the corrosion resistance of titanium.

The microorganisms have several virulence agents and release volatile sulfur compounds, such as methyl mercaptan, hydrogen sulfide, dimethyl sulfide. These virulence agents can influence titanium corrosion, depending on their concentration and pH. Titanium implants can have mechanical and biological complications due to corrosion, including the initiation of peri-implantitis by corrosion, mechanical stress, and bacteria, which can ultimately contribute to implant failure.

Corrosion fatigue fracture is another outcome of implant corrosion. Bacterial corrosion can produce weak points that progress to fatigue cracks, which can propagate with chewing cycles. When the crack becomes sufficiently large, the implant material may fail to withstand a typical load, resulting in implant fractures.

Use of antibacterial coatings has been explored as a method for improving implant lifetime. Even use of different metals in implants can have significant effects on bacterial growth. Many groups have explored the addition of charged metallic particles to implants (copper, silver, magnesium, etc.); however, a concern with all these implants is diffusion of these ions to the surrounding tissue.

Despite advances in implant coating research, there is still a scarcity of coatings that are potent, efficacious, and selective inhibitors of the growth of pathogenic bacteria and biofilms consisting thereof, while remaining biocompatible as well as intact for the lifetime of the coatings. Furthermore, it would be advantageous to minimize corrosion of dental material surfaces as well to minimize bacterial proliferation and adhesion on these surfaces. These needs and other needs are satisfied by the present disclosure.

SUMMARY

In accordance with the purpose(s) of the present disclosure, as embodied and broadly described herein, the disclosure, in one aspect, relates to protective, anti-bacterial coatings for medical implants and methods of making the same. Also disclosed herein are methods for improving the antibacterial properties of a medical device coated with silicon carbide (SiC) or titanium nitride (TiN). Further disclosed herein is a medical device including an anti-microbial layer prepared by the disclosed methods.

In one aspect, disclosed herein is a medical apparatus that includes a substrate and a silicon carbide coating or a titanium nitride coating. In some aspects, the substrate can be a ceramic material, a glass-ceramic material, a zirconia material, a metal, or a combination thereof. In some aspects, the silicon carbide coating or titanium nitride is quaternized to increase its antimicrobial properties. Also disclosed herein are methods for quaternizing the silicon carbide or titanium nitride.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 2A shows atomic force microscopy (AFM) images of surface topography of non-coated samples with 10 μm amplification. FIG. 2B shows AFM images of surface topography of SiC coated surfaces with 10 μm amplification.

FIG. 12A shows bacterial corrosion on a non-coated ceramic surface. FIG. 12B shows lower bacteria counts and much less corrosion on a SiC-coated ceramic implant surface compared to a non-coated surface.

FIG. 14A: a non-coated sample at 0 days; FIG. 14B: a non-coated sample held at pH 10 for 30 days; FIG. 14C: a non-coated sample held at pH 2 for 30 days; FIG. 14D: a coated sample at 0 days; FIG. 14E: a coated sample held at pH 10 for 30 days; and FIG. 14F: a coated sample held at pH 2 for 30 days.

FIGS. 21A and 21F: non-coated; FIGS. 21B and 21G: coated with TiN; FIGS. 21C and 21H: coated with qTiN; FIGS. 21D and 21I: coated with SiC; FIGS. 21E and 21J: coated with qSiC.

Figure 1:
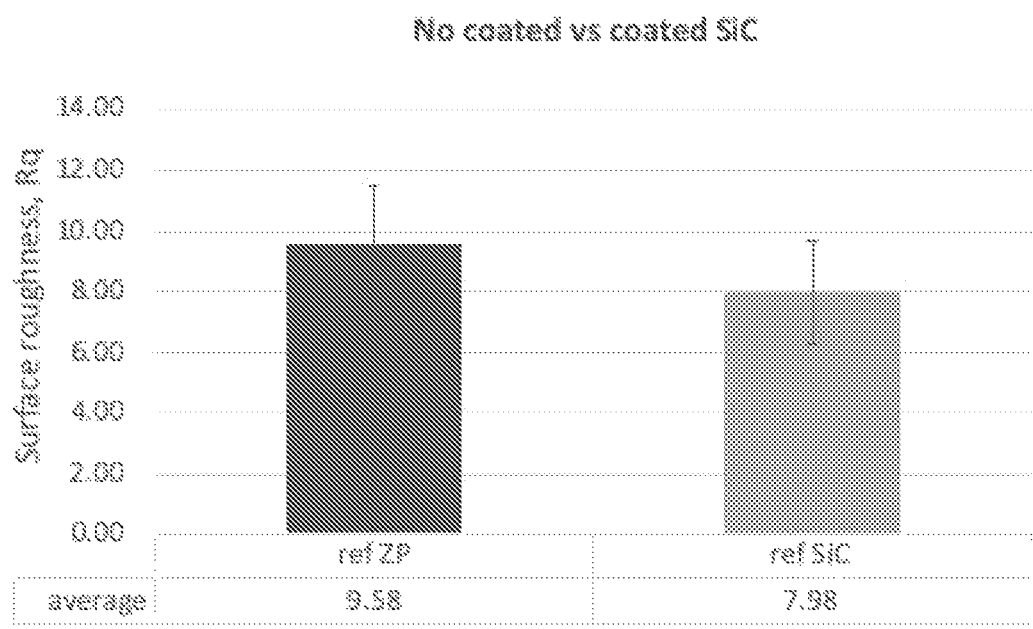
FIG. 1 shows representative data for roughness means and standard deviations for non-coated (ref) and representative coated (ref SiC) samples. Data represent a single 10 μm×10 μm image.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a bacterial species," "a metal oxide," or "an alkyl halide," includes, but is not limited to, mixtures of two or more such bacterial species, metal oxides, or alkyl halides, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a alkyl halide refers to an amount that is sufficient to achieve the desired improvement in the property modulated by the formulation component, e.g. achieving the desired level of quaternization of a surface nitrogen species. The specific level in terms of wt % in a composition required as an effective amount will depend upon a variety of factors including the amount and type of alkyl halide, roughness and composition of substratum surface, and end use of the medical apparatus to be coated.

As used herein, the terms "optional" or "optionally" means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

A "biofilm" as used herein is a collection of microorganisms wherein the cells stick to each other and also, typically, to a surface. Biofilms generally include an extracellular matrix composed of polymeric substances including polysaccharides, proteins, lipids, and even nucleic acids. A "monomicrobial" biofilm consists of only one species of microorganism. A "polymicrobial" biofilm consist of two or more species of microorganism. An "oral biofilm" as used herein refers to a bacterial biofilm coating on the teeth (e.g., dental plaque), gums, or a dental implant or device, or at the interfaces between these elements. In some aspects, oral biofilms cause damage to both the oral cavity and to implanted devices and other dental devices (e.g., braces brackets, wires, and the like).

"Enamel" as used herein is a tissue making up the outer layer of the exposed or external surface of human teeth. Enamel is typically hard, white or off-white, and mineralized. In some aspects, biofilms can form on enamel. In other aspects, the microorganisms making up biofilms can cause damage to tooth enamel. Enamel is composed primarily of hydroxyapatite.

Materials that are "biocompatible" as used herein refers to materials that do not cause harm to living tissue. Biocompatible materials also do not stimulate an immune response. In one aspect, the coatings and surfaces disclosed herein are biocompatible. Meanwhile, "cytotoxic" materials cause harm or damage to cells and may cause cell death.

As used herein, "substratum" or "substratum surface" refers to the surface on which a biofilm grows and/or forms. In one aspect, substratum properties including roughness, hydrophobicity, charge, and the like may affect cell attachment.

"Supragingival" as used herein refers to plaque or tartar (i.e., calculus) above the gum line (gingiva), or to the location of a dental restoration above the gum line. By contrast, "subgingival" refers to these features or phenomena below the gum line.

As used herein, "water contact angle" or WCA is a measure of surface hydrophobicity. WCA is measured through liquid, where a liquid-vapor interface meets a solid surface. For WCA above 90°, it is considered that water does not wet the substrate (i.e., the substrate is hydrophobic). For WCA below 90°, it is considered that water wets the substrate (i.e., the substrate has some degree of hydrophilicity) and/or that adhesion or spreading occurs.

As used herein, "peri-implantitis" refers to a destructive, inflammatory disease of the gums (gingiva) and surrounding bone structure around a dental implant. Peri-implantitis is an infectious condition that results in bone loss and can be treated using various treatments ranging from antibiotic and/or antiseptic treatments, mechanical debridement, and/or surgery.

"Perimucositis," meanwhile, refers to an inflammatory disease of the gums around a dental implant that is not associated with bone loss. Perimucositis may occur during healing after surgical placement of an implant and can usually be treated with self-care or home care or by a dental professional using non-surgical and/or non-invasive procedures.

"Pen-implant disease" can refer to either perimucositis and/or peri-implantitis.

"Quaternized" as used herein refers to a surface coating that has been chemically-modified to include quaternary ammonium species. A surface to be quaternized can include nitrogen as part of the coating or may be modified after formation to include nitrogen for quaternization.

"Surface roughness" as used herein is abbreviated "Rq" and can be calculated by a technique such as, for example, atomic force microscopy. In one aspect, Rq represents the root mean square average of height deviation from the mean AFM image data plane.

"Developed interfacial area ratio" as used herein is abbreviated "Sdr" and is a parameter expressed as the percentage of an areas additional surface area contributed by texture as compared to the planar definition area. In one aspect, Sdr of a completely level surface is 0, while a higher value for Sdr indicates the surface has texture and, thus, additional surface area when compared to a level surface of the same planar area.

The term "prevent" as used herein is defined as eliminating or reducing the likelihood of the occurrence of one or more problems associated with microbial contact (e.g. preventing corrosion of titanium devices in the oral cavity). The term "reduce" as used herein is defined as decreasing the severity of one or more problems by applying a disclosed coating (e.g., reducing the amount of titanium that leaches from a medical apparatus, or reducing biofilm formation, or the like) when compared to not applying the disclosed coating. The term "improve" as used herein is defined as enhancing or increasing a property of a substrate or medical apparatus by applying a disclosed coating (e.g., attaining a higher level of biofilm inhibition, corrosion resistance, or the like) when compared to the same substrate or medical apparatus in the absence of the disclosed coating.

As used herein, "antimicrobial" refers to a property of an object, material, or composition that kills, reduces reproduction and/or growth of, or treats, prevents, reduces, or corrects a problem associated with, one or more microbial species. Thus, in one aspect, an antimicrobial coating can kill a microbial species, or reduce the likelihood of that microbial species forming a biofilm, or reduce corrosion damage caused by the microbial species on a medical apparatus such as, for example, a dental or joint implant. In one aspect, the microbial species can be a bacterium or a fungus. In another aspect, the microbial species can be selected from typical oral microbiota such as, for example *Streptococcus salivarius, Streptococcus mutans, Streptococcus sanguinis, Porphyromonas gingivalis*, another bacterium, or any combination thereof.

Medical Implants and Devices

In one aspects, the coatings disclosed herein are useful for any dental or medical device or appliance. In a further aspect, the coatings can be used on ceramic crowns, metal crowns, orthodontic brackets, orthodontic wires, posts for restoring endodontically treated teeth, dental implants, removable denture metal frameworks, implant-supported bars for denture retention, removable denture attachments, and/or joint implants or devices including, but not limited to, hip, knee, temporomandibular joint, and elbow replacements, and the like.

Substrate Materials and Coating Layers

In a further aspect, the coatings disclosed herein are SiC or TiN coatings. In another aspect, the coatings can be applied over metals, metal-based compounds, and/or metal oxides including, but not limited to, layers of Ti, TiN, TiC, $TiO_2$, $Ti_3O_5$, $Ti_2O_3$, TiO, $Ti_6Al_4V$, $TiSiC_2$, SiNO, $Al_2O_3$, $HfO_2$, $HfSiO_4$, $Y_2O_3$, $ZrO_2$, $La_2O_3$, SrO, $Ta_2O_5$, $ZrSO_4$, and combinations thereof.

In one aspect, disclosed herein are devices made of a substrate material including, but not limited to, a ceramic material, a glass-ceramic material, a zirconia-based material, or metal. In one aspect, the ceramic material, glass-ceramic material, or zirconia is selected from 3Y-TZP zirconia, 12Ce-TZP/$Al_2O_3$ zirconia, alumina ($Al_2O_3$), spinel ($MgAl_2O_4$), lithium disilicate ($Li_2Si_2O_5$), feldspar ((Na,K) $AlSi_3O_8$), leucite ($KAlSi_2O_6$), fluorapatite ($Ca_5(PO_4)_3F$), or a combination thereof. In some aspects, the substrate is fluorapatite. In another aspect, the metal can be selected from gold, a gold alloy, stainless steel, a cobalt-chromium alloy, titanium, a Ti-6Al-4V alloy, a nickel-chromium alloy, an iron-chromium-nickel alloy, platinum, iridium, tantalum, tungsten, or a combination thereof. In some aspects, the substrate can be coated with a metal, a metal-based compound, or a metal oxide as disclosed herein. In a further aspect, the titanium-based or metal oxide layer can be modified with an additional passivating or $SiO_2$ layer prior to application of the SiC or TiN coating. In some aspects, the SiC or TiN coatings can be further quaternized as disclosed herein.

In another aspect, prior to addition of any coating, the substrate material can be treated using a surface treatment to improve adhesion and/or abrasion resistance prior to coating. In a further aspect, the surface treatment can be acetone cleaning in an ultrasonic bath, an isopropyl alcohol rinse with compressed nitrogen dry, ozone treatment to remove surface carbon contamination, or a combination thereof.

Also disclosed herein are coatings produced by the disclosed methods and metal apparatuses including the coatings.

SiC and qSiC Coatings

In a further aspect, a SiC film can be deposited on the substrate material using a method such as, for example, chemical vapor deposition. Further in this aspect, methane ($CH_4$) and silane ($SiH_4$) can be used as the starting materials for chemical vapor deposition.

In various aspects, the SiC or qSiC coating can have a thickness of from about 50 μm to about 1000 μm. In a further aspect, the SiC or qSiC coating can have a thickness of about 50 μm, about 100 μm, about 150 μm, about 200 μm, about 250 μm, about 300 μm, about 350 μm, about 400 μm, about 450 μm, about 500 μm, about 550 μm, about 60 μm, about 650 μm, about 700 μm, about 750 μm; or any combination of the foregoing values; or any range comprising a foregoing value as a lower limit and a second foregoing value as an upper limit of the range.

Also disclosed are medical apparatuses including the disclosed SiC and qSiC coatings.

TiN and qTiN Coatings

In one aspect, disclosed herein is a method for forming a coating on a medical apparatus or other substrate, the method including the step of sputter coating an inert gas with a TiN target to form a TiN layer. In another aspect, the inert gas can be argon. In another aspect, sputter coating can be accomplished using a platen bias of about 30 V.

In one aspect, the method further includes reacting nitrogen atoms in the TiN layer with an allyl halide to quaternize the nitrogen atoms. In another aspect, the allyl halide can be allyl bromide, allyl chloride, allyl iodide, or any combination thereof.

In various aspects, the TiN or qTiN coating can have a thickness of from about 20 to about 200 nm thick, or of about 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, or about 200 nm, or a combination of any of the foregoing values, or a range encompassing any of the foregoing values. In one aspect, the TiN or qTiN coating is about 50 nm thick.

Also disclosed are medical apparatuses including the disclosed TiN and qTiN coatings.

In various aspects, the present disclosure relates to a substrate material that is a metal, e.g., titanium, vanadium, a titanium alloy, or a vanadium alloy, that comprises a coating, e.g., a passivation coating. Thus, in a further aspect, the present disclosure pertains to a medical device having a substrate material comprising a metal, and further comprising a coating thereon, e.g., $SiO_2$, that is further coating thereon with a disclosed SiC or qSiC coating.

Adhesion of Microbial Species to Solid Surfaces

*Streptococcus* Species

In one aspect, the adhesion of streptococci to solid surfaces has been described as a two-step process. In a further aspect, the first step of this process is influenced by macroscopic substratum properties including surface roughness and surface free energy. In some aspects, high substratum surface roughness has been associated with increased plaque formation in vivo. Without wishing to be bound by theory, the initial adhesion of microorganisms is thought to begin at locations that provide shelter against shear forces. In another aspect, surfaces with high surface free energy are associated with microbial adherence in vitro and in vivo, and furthermore, bacteria with high cell surface free energy adhere preferentially to surfaces with high surface free energy.

In one aspect, bacterial adhesion to a substrate and initial biofilm composition are related to topography, surface hydrophobicity, and communication among existing microorganisms. In one aspect, the coated SiC surfaces disclosed herein are more hydrophobic than non-coated surfaces. In a further aspect, atomic force microscopy (AFM) images of coated and non-coated surfaces as disclosed herein shows differences in topography.

In one aspect, *S. mutans, S. salivarius*, and *S. sanguinis* are useful model organisms for determining bacterial adhesion to surfaces. In one aspect, these species are early colonizers of supragingival biofilm (i.e., within the first 8 hours of formation) and are present in large quantities in oral biofilms. In a further aspect, the SiC-coated fluorapatite glass-ceramic surfaces disclosed herein demonstrate lower adhesion of these two species. In a still further aspect, significant reductions in the number of CFU/mL are observed for monomicrobial biofilms of *S. mutans* and *S. sanguinis* on the SiC-coated surfaces disclosed herein. Without wishing to be bound by theory, SiC-coated surfaces are more hydrophobic than non-coated surfaces, as well as being slightly smoother; it is believed these properties may be related to observed differences in bacterial adhesion.

*Porphyromonas gingivalis* Adhesion

In one aspect, quaternization of SiC surfaces reduces the biofilm coverage by species typically found in patient oral cavities such as, for example, *P. gingivalis*. In a further aspect, uncoated substrates exhibit significantly higher biofilm coverage after 4 hours of incubation as opposed to qSiC coated substrates.

Antimicrobial Properties

In some aspects, the SiC, qSiC, TiN, and qTiN coatings disclosed herein exhibit antimicrobial properties. In another aspect, the coatings can reduce microbe-induced corrosion of the medical apparatus and/or surfaces disclosed herein.

In one aspect, disclosed herein is a method for improving the antimicrobial properties of the SiC coatings described herein. In a further aspect, the method involves reacting the SiC layer with a plasma to add nitrogen atoms to the SiC layer and reacting the nitrogen atoms with an alkyl halide in a solvent to further quaternize the nitrogen atoms. In one aspect, the reaction takes about one hour to complete. In one aspect, the plasma is an ammonia plasma. In a further aspect, the coated, quaternized substrates can be rinsed using isopropyl alcohol, followed by a rinse with deionized water, to remove excess solvents, reagents, byproducts, and the like. In some aspects, the alkyl halide can be allyl chloride, allyl bromide, or allyl iodide. In other aspects, the coatings disclosed herein include alkyl halide or alkenyl halide derivatives such as, for example, derivatives of C1-C6 alkyl and/or alkenyl halides. In a further aspect, the alkyl halide or alkenyl halide derivative is a quaternary ammonium moiety. In another aspect, disclosed herein is a medical apparatus that includes a quaternized SiC (qSiC) layer prepared by the disclosed methods. In a further aspect, contact angle measurements can be conducted as disclosed herein in order to verify successful quaternization. In a still further aspect, X-ray photoelectron spectroscopy can be used to verify changes to chemical composition of the surfaces of the substrates as disclosed herein.

In another aspect, disclosed herein is a method for improving the properties of a medical apparatus coated with a titanium nitride (TiN) layer, the method including at least the step of reacting the nitrogen atoms in the TiN with an allyl halide. Further in this aspect, the allyl halide can include allyl bromide, allyl chloride, allyl iodide, or any combination thereof. In any of these aspects, the medical apparatus can be partially or wholly constructed from titanium.

Biocompatibility of Surfaces and Coatings

In one aspect, ceramic materials with different compositions may have different outcomes with respect to cell viability, with some materials enhancing cell viability and other materials contributing to cell death, shrinkage, or other negative outcomes. In one aspect, fluorapatite glass-ceramic or titanium with or without SiC coating or TiN coating exhibits no cytotoxicity. In another aspect, fluorapatite glass-ceramic is biocompatible. In one aspect, biocompatibility of materials can be evaluated based on the presence or absence of a direct interaction between the materials and cells growing on or near the materials. In a further aspect, human periodontal ligament cells can adhere to both non-coated and SiC-coated fluorapatite glass-ceramic, or to both non-coated and SiC-coated or TiN coated titanium, indicating biocompatibility.

In another aspect, qSiC and qTiN coatings are also biocompatible. In one aspect, cells such as, for example, human osteoblasts (NHOst cells) cultivated in the presence of qSiC or qTiN coated substrates proliferate in the presence of both coated and non-coated substrates, indicating biocompatibility and lack of cytotoxicity.

Durability of Surfaces

Ceramic Surfaces

In one aspect, the SiC coatings disclosed herein are useful for minimizing corrosion and increasing fracture resistance on ceramic substrates including ceramic veneers. In another aspect, the SiC coatings disclosed herein are wear-resistant. In still another aspect, the SiC coatings disclosed herein can be matched to existing tooth shades through manipulation of their refractive indices and extinction coefficients.

In another aspect, the SiC coatings disclosed herein exhibit anti-corrosive properties. In a further aspect, fluorapatite or other substrates coated with the SiC coatings disclosed herein exhibit less weight loss than uncoated substrates under extended exposure to acidic (e.g., pH 2) or basic (e.g., pH 10) pH for an extended period of time such as, for example, 15 days or 30 days. In one aspect, substrates coated with the disclosed coatings exhibit weight loss of less than about 1%, or of less than about 0.9, 0.8, 0.7, 0.6, or 0.5% of an initial weight after 30 days of exposure to an acidic environment, or a combination of any of the foregoing values, or a range encompassing any of the foregoing values.

Titanium Surfaces

In one aspect, the SiC and TiN coatings, both quaternized and non-quaternized, disclosed herein, when applied to a titanium substrate such as, for example, a medical apparatus, assist in preventing the breakdown of the titanium substrate in the presence of one or more microbial species. In one aspect, following at least 30 days of exposure to one or more microbial species, coated substrates and apparatuses release less than about 35 ppb titanium into the surrounding medium, or less than about 30, less than about 25, less than about 20, less than about 15, less than about 10, or less than about 5 ppb of titanium into the surrounding medium, or a combination of any of the foregoing values, or a range encompassing any of the foregoing values. In another aspect, substrates and medical apparatuses having the disclosed coatings do not exhibit a net weight change after 30 days of exposure to one or more microbial species.

In another aspect, following at least 30 days of exposure to one or more microbial species, coated substrates and apparatuses have a surface roughness (Rq) as determined by AFM of less than about 55 mm, less than about 50 mm, less than about 45 mm, less than about 40 mm, less than about 35 mm, less than about 30 mm, less than about 25 mm, or less than about 20 mm, or a combination of any of the foregoing values, or a range encompassing any of the foregoing values. In another aspect, percent increase in Rq of the substrate or medical apparatus is less than about 15%, 14%, 13%, 12%, 11%, or less than about 10% compared to Rq of the substrate or medical apparatus prior to exposure to the one or more microbial species.

Medical Apparatus

In one aspect, disclosed herein is a medical apparatus containing or including the disclosed substrates, surfaces, and/or coatings. In another aspect, the medical apparatus can be a dental prosthesis such as, for example, a crown, a post for restoring endodontically treated teeth, a tooth veneer, a partial denture, a palatal obturator, a removable metal framework for dentures, implant-supported bars for denture retention, a removable denture attachment, an orthodontic appliance, or a combination thereof. In another aspect, the medical apparatus can be a replacement joint such as, for example, a hip joint, a knee joint, a temporomandibular joint, or an elbow joint.

Properties of the Medical Apparatus

In some aspects, the disclosed medical apparatuses may have additional desirable properties. In one aspect, the medical apparatuses disclosed herein have a water contact angle of greater than about 60°, or of greater than about 60°, 65°, 70°, 75°, 80°, 85°, or about 90°, or a combination of any of the foregoing values, or a range encompassing any of the foregoing values. Exemplary methods for measuring the water contact angle are provided in the Examples.

In another aspect, the medical apparatuses disclosed herein have a carbon content of less than about 5 wt % after five years of service, or of less than about 4.9, 4.8, 4.7, 4.6, 4.5, 4.4, 4.3, 4.2, 4.1, or about 4 wt % after five years of service, or a combination of any of the foregoing values, or a range encompassing any of the foregoing values.

In still another aspect, the disclosed medical apparatuses have a biofilm coverage of less than about 20% after 24 hours of exposure to at least one biofilm-forming microbial species, or of less than about 20, 19.5, 19, 18.5, 18, 17.5, 17, 16.5, 16, 15.5, or less than about 15%, or a combination of any of the foregoing values, or a range encompassing any of the foregoing values.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Specimen Preparation

Fluorapatite Disks

Eighty fluorapatite glass-ceramic disks (12×2 mm) were prepared for SiC-coated and non-coated groups. Disks were subjected to three different surface treatments to improve adhesion and abrasion resistance prior to coating. These processes include: (1) acetone cleaning in an ultrasonic bath; (2) isopropyl alcohol rinse and compressed nitrogen dry and; (3) ozone treatment to remove surface carbon contamination.

SiC film depositions were performed with a Plasma Enhanced Chemical Vapor Deposition (PECVD, Plasma-Therm 790, Saint Petersburg, Fla.) system. Methane ($CH_4$) and silane ($SiH_4$) were used for silicon carbide deposition. The PECVD system has a load lock and a parallel plate deposition configuration with a shower head. The deposition temperature was kept at 350° C. and the deposition pressure was maintained to 1100 mTorr. The rf power was 400 W and the SiC deposition rate was 340 Å/min.

Titanium Disks

Titanium rods at high purity (0.9999, TMS Titanium, Poway, Calif., USA) were cut with a Buehler Isomet 2000 into disks and polished to a grit size of 600 to 11×2 mm. First, the disks were cleaned with acetone in an ultrasonic bath, then rinsed with isopropyl alcohol and dried with compressed nitrogen. The disks were then treated with ozone to remove any surface carbon contamination.

Five experimental groups (n=60) were included in studies with titanium disks: (1) non-coated titanium disks as the reference group, (2) titanium nitride coated titanium disks (TiN), (3) quaternized titanium nitride coated titanium disks (qTiN), (4) silicon carbide coated titanium disks (SiC), and (5) quaternized silicon carbide coated titanium disks (qSiC).

Example 2: Coating Process

Forty-eight pre-cleaned titanium disks were coated with either TiN, qTiN, SiC, qSiC (4 disks per group). The remaining 12 disks were left as controls.

To coat samples with 200 nm of SiC, a plasma-enhanced chemical vapor deposition system (PECVD, PlasmaTherm 790, Saint Petersburg, Fla.) was used. Gas precursors used for SiC deposition were methane ($CH_4$) and silane ($SiH_4$) at a deposition temperature of 300° C. Prior to quaternizing the SiC surface, the SiC was exposed to a 400 W ammonia plasma for 30 minutes at 300° C. to incorporate nitrogen into the surface.

Quaternized SiC (qSiC) samples were prepared by immersing the ammonia plasma-treated samples into a solution containing acetonitrile (25 mL) and allyl bromide (100 µL) for 1 hour to quaternize the surface nitrogen. After removing the samples from the quaternization solution, excess solvent and reagent were removed using rinses of isopropanol and deionized water (Fisher Scientific, Pittsburgh, Pa.).

To coat samples with 50 nm of titanium nitride (TiN), a Kurt J. Lesker CMS 18 (Jefferson Hills, Pa.) sputter system was used. An allowed TiN target was used in pure Ar ambient at room temperature. A platen bias of 30 V was applied to during TiN deposition to promote film regularity.

Quaternization of the surface nitrogen was performed using the same procedure as for quaternized SiC substrates to yield a quaternized TiN surface. No plasma treatment was required for TiN samples since the surface already contained nitrogen that could be quaternized.

Example 3: Atomic Force Microscopy (AFM)

Topographies of non-coated and coated with SiC samples were evaluated using a SPM-AFM system (Bruker/Veeco/Digital Instruments NanoScope V) operating in tapping mode and using a silicon AFM probe (RTESP-300, Bruker, Billerica, Mass., USA) with radius less than 10 nm and resonance frequency of 200 to 400 kHz. The images (10 µm×10 µm) obtained were treated using the NanoScope Analysis software.

Figure 2A:
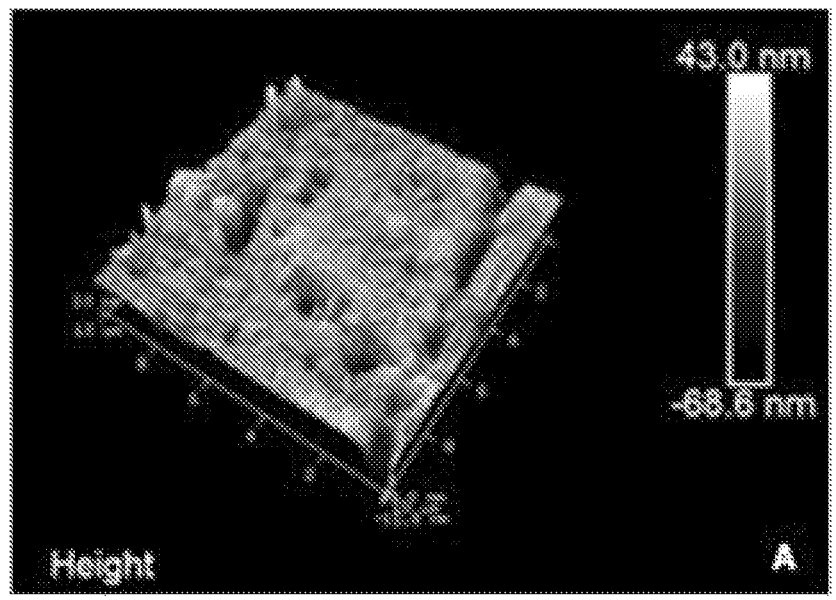
FIGS. 2A-2B show representative atomic force microscopy (AFM) images of surface topography for non-coated and representative coated samples.
Figure 2B:
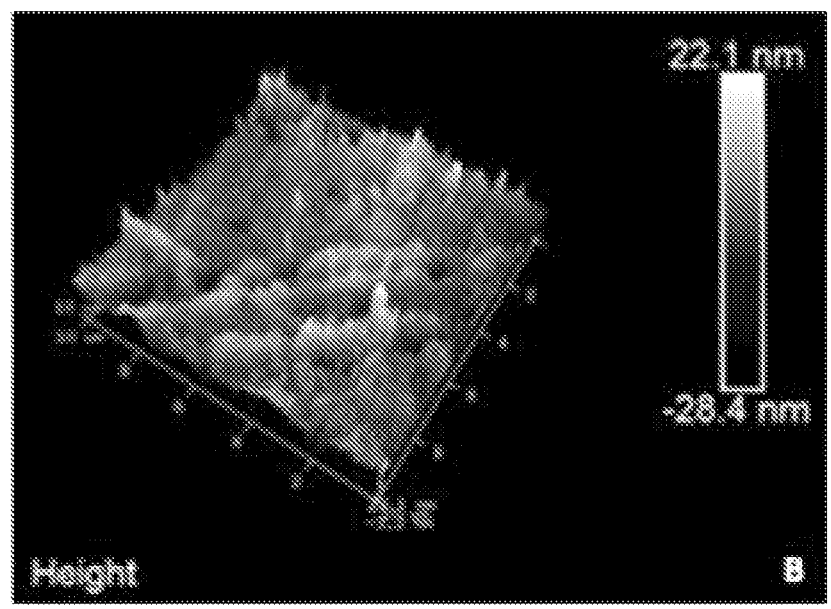

AFM analysis showed an irregular surface topography in non-coated samples, while the coating samples were slightly more homogeneous (p>0.05) (FIGS. 1, 2A-B).

Example 4: Water Contact Angle Measurements

Water contact angle (WCA) was assessed on the neutralized non-coated and coated SiC surfaces (neutralized up to pH 6.0). Static contact angles were assessed by the sessile drop method with a contact angle goniometer (Krüss DSA 10, Hamburg, Germany) equipped with video capture. The automatic dosing feature of the DSA 10 dispenses a water drop on the non-coated and coated SiC surfaces and the needle is manually withdrawn. Images were captured after contact of a droplet with the surface by a camera leveled with the surface. Contact-angle measurements were analyzed by the circle fitting profile available with the DSA 10 imaging software. Three separate measurements were made on each sample at different locations.

WCA was different for the non-coated and coated surfaces, with coated SiC surfaces presenting higher contact angles than non-coated surfaces (p>0.05). Data are presented in Table 1 below.

TABLE 1

Mean Contact Angle Measurements on Coated SiC Surfaces vs. a Non-coated Surface.

| Ceramic Sample | Contact Angle (± SD) |
|---|---|
| Non-Coated | 46° ± 2° |
| Coated SiC | 60° ± 1° |

Example 5: Bacterial Growth

Twenty-four ceramic specimens of each group were sterilized in an autoclave (121° C., 60 min) and each one was distributed on a sterile 24-well plate. Antimicrobial activity was evaluated using reference strains (ATCC—American Type Culture Collection) of *Streptococcus mutans* (ATCC 35688) and *Streptococcus sanguinis* (ATCC BAA-1455). Strains were kept frozen (−80° C.) in Brain Heart Infusion broth (BHI—Himedia, Mumbai, India) with 20% glycerol.

Monomicrobial and polymicrobial biofilms of *S. sanguinis* and *S. mutans* were evaluated. The strains were initially grown on solid medium and afterwards in liquid medium (BHI agar and broth) for 24 h at 37° C. (5% $CO_2$ for *S. mutans*). Each microbial suspension was centrifuged at 4700 rpm for 10 min (MPW-350, Warsaw, Poland), the supernatant was discarded, and the pellet was suspended in saline solution. This step was performed twice to minimize the quantity of debris. The microbial suspension was adjusted to $10^7$ CFU/mL and 100 μL was added in wells of a 24 well-plate with 1 mL medium and ceramic specimens (coated and non-coated). The plate was maintained in shaking inside the incubator (37° C.; 75 rpm) for 90 min, for initial adhesion of the biofilms, after which 50 μL of each standardized inoculum (*S. sanguinis* and *S. mutans*) was added. Subsequently, the supernatant was discarded and 1 mL of BHI broth was added for development of the biofilm.

Colony Forming Units

After 24 h of incubation, the ceramic samples were removed and placed inside a microcentrifuge tube with ringer solution. The biofilm was disaggregated using an ultrasonic homogenizer (Sonopuls HD 2200—Bandelin Electronic, Berlin, Germany) with 25% power for 30 s. The generated microbial suspension was serially diluted (1:10) and 100 μL were seeded on BHI agar for each respective sample. After 48 h of incubation, the concentration of colony forming units (CFU) per mL was determined by visual counting.

Fluorescence Assay

After 24 h of incubation, the culture medium was removed and adhered bacteria were then stained with SYTO® 9 dye (Live/Dead BacLight Bacterial Viability Kit, ThermoFisher Scientific) according to the manufacturer's instructions. Fluorescence images of the live bacteria were recorded in a fluorescence microscope (Zeiss Imager-A2, Germany) and analyzed using ImageJ software. Bacteria coverage percentages were averaged over five random areas on each filter specimen (n=8).

Scanning Electron Microscopy

After 24 h of incubation, the culture medium was removed and the polymicrobial biofilm adhered to the samples was fixed in a solution of 3% glutaraldehyde, 0.1 M sodium cacodylate, and 0.1 M sucrose for 45 min. Samples were soaked for 10 min in a buffer solution of 0.1 M sodium cacodylate and 0.1 M sucrose. Sample surfaces and cells were processed in serial ethanol dehydrations for 10 min each and dehydrated in hexamethyldisilazane (HDMS) before being stored in a desiccator until SEM imaging. The samples were then sputter-coated with a palladium-gold alloy (Polaron SC 7620 Sputter Coater, Quorum Technologies, Newhaven, UK) at a thickness of 10 nm to reduce charging effects during SEM analysis (10-15 mA under a vacuum of 130 mTorr). The SEM was operated at 5 kV, spot 3 to 6 (FEI NOVA 430).

Results

Figure 3:
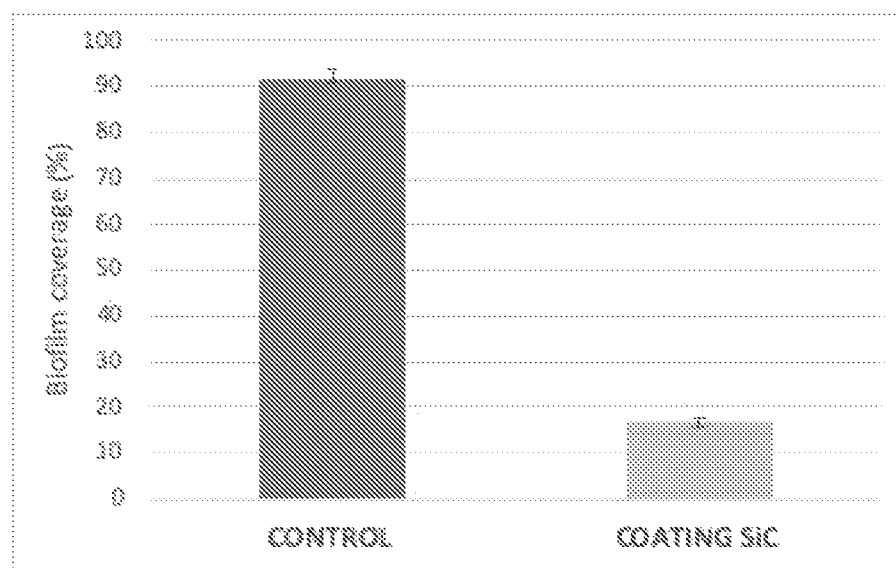
FIG. 3 shows representative data for biofilm coverage of S. mutans and S. sanguinis after 24 h of culture on non-coated (control) and representative coated surfaces as described herein.
Figures 4A, 4B, 4C, 4D, 4E, 4F:
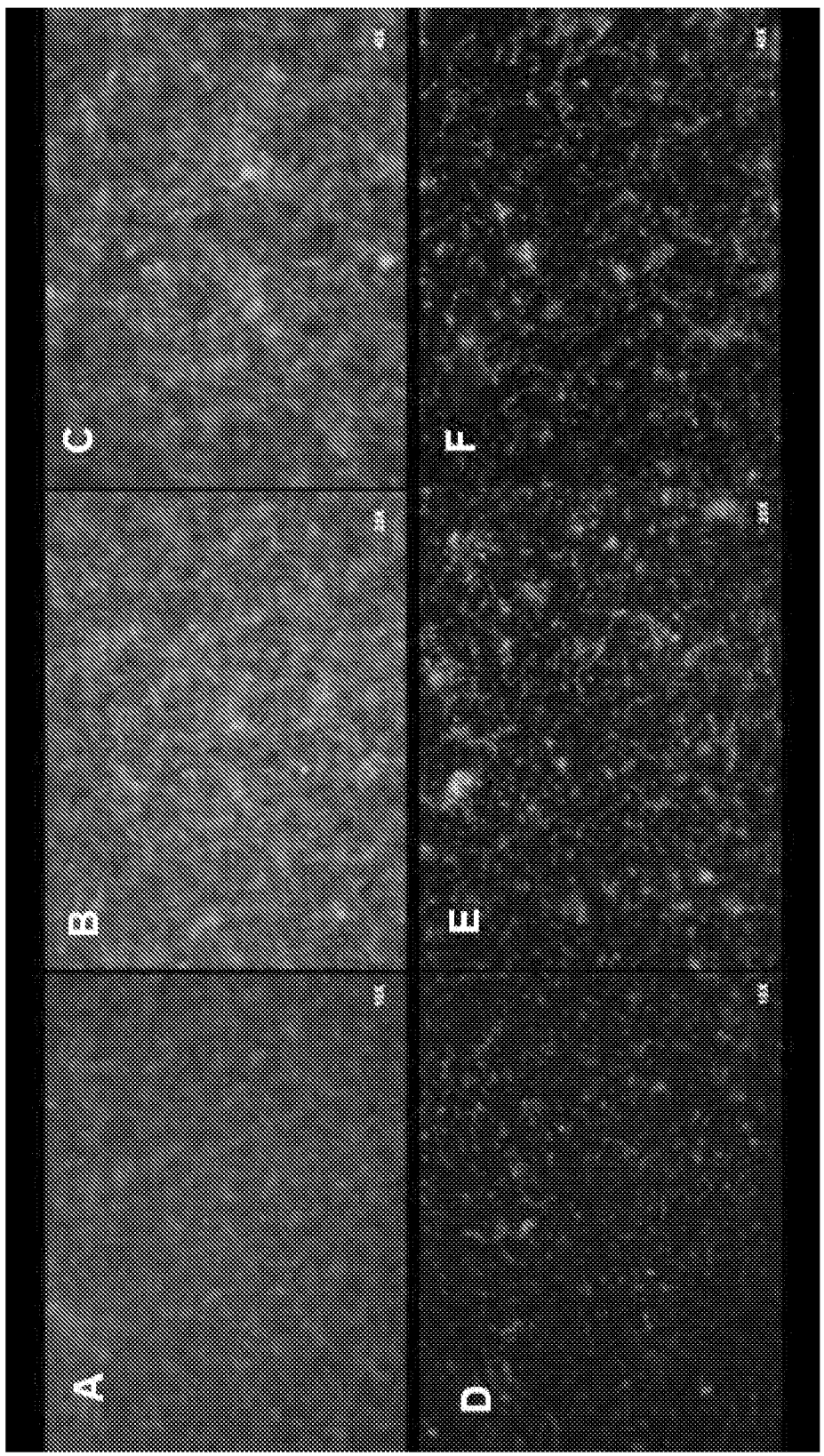
FIGS. 4A-4F shows fluorescence live images of S. mutans and S. sanguinis cultured for 24 h on either non-coated (FIGS. 4A-4C) or SiC coated (FIGS. 4D-4F) surfaces. SYTO® dye was used to stain, with living bacteria displaying as green. All images include both S. mutans and S. sanguinis.
Figures 5A, 5B, 5C, 5D, 5E, 5F, 5G, 5H:
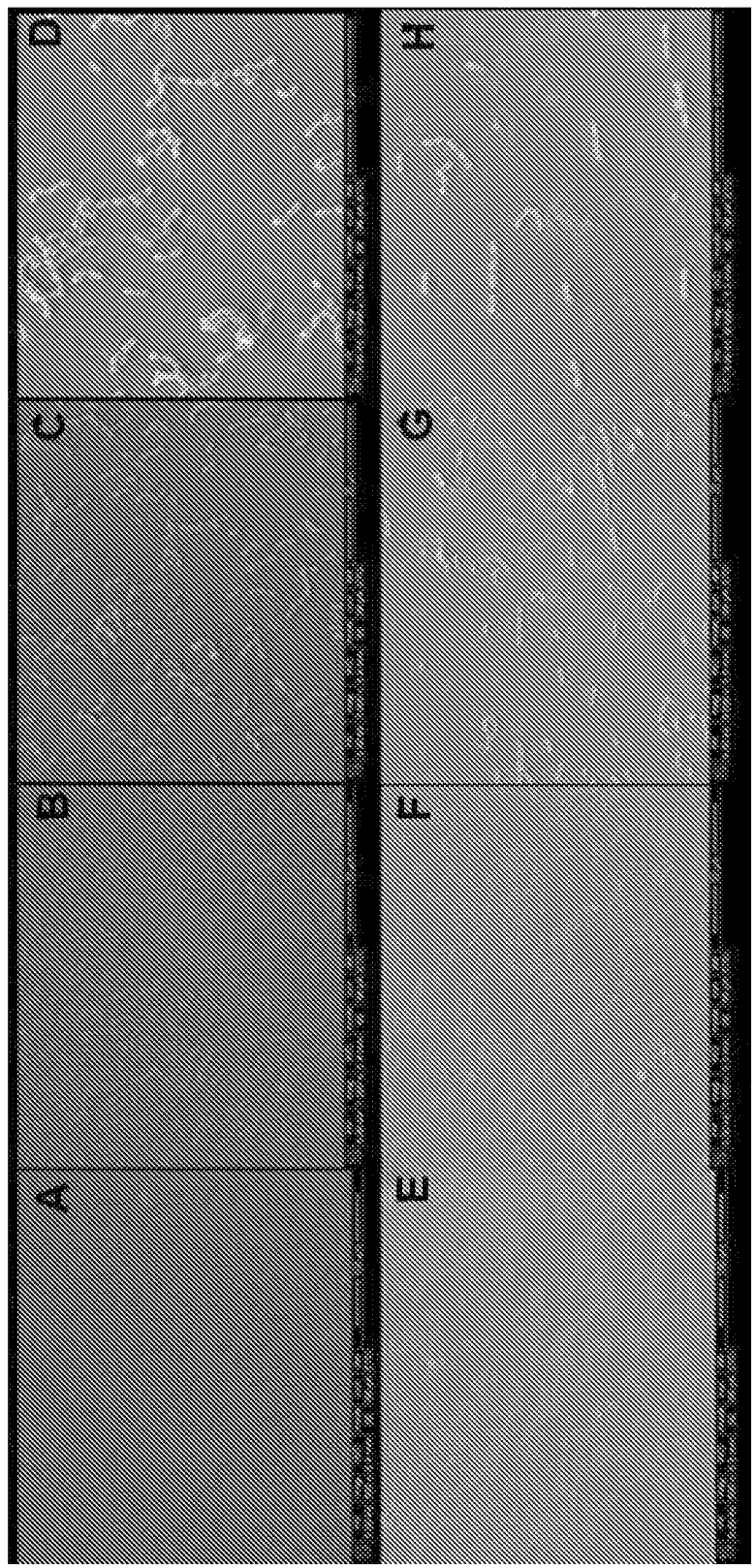
FIGS. 5A-D show SEM images of cell adhesion of S. mutans and S. sanguinis after 24 h cultivation on a non-coated surface.
FIGS. 5E-H show SEM images of cell adhesion on SiC-coated surfaces. All images include both S. mutans and S. sanguinis.

After 24 h, the area of polymicrobial biofilm (*S. mutans* and *S. sanguinis*) was less on the ceramic coating with SiC; coated samples showed a biofilm coverage of 16.9%, whereas uncoated reference samples showed a significantly higher biofilm coverage of 91.8% ($p<0.0001$) (FIG. 3). Fluorescence microscopy confirms higher biofilm formation on the control group than the coated group (FIGS. 4A-4F). The SEM images mirror the results from the live assays, showing a reduction in the number of adherent bacteria on the coated group for *S. mutans* and *S. sanguinis* after 24 h of culture (FIGS. 5A-5H).

Figure 6A:
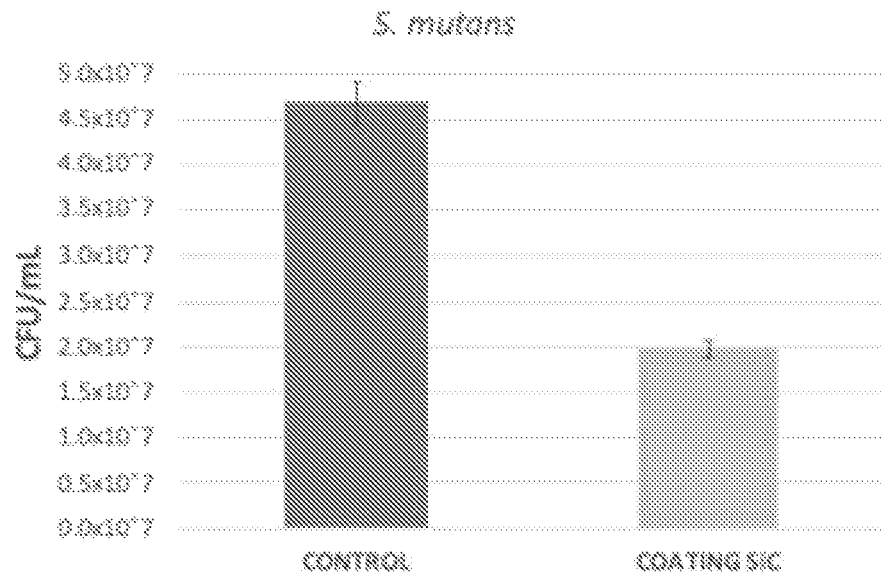
FIGS. 6A-6B shows mean (±standard deviation) of colony forming units (CFU)/mL of monomicrobial biofilms of S. mutans (FIG. 6A) and S. sanguinis (FIG. 6B) for non-coated and SiC-coated surfaces.
Figure 6B:
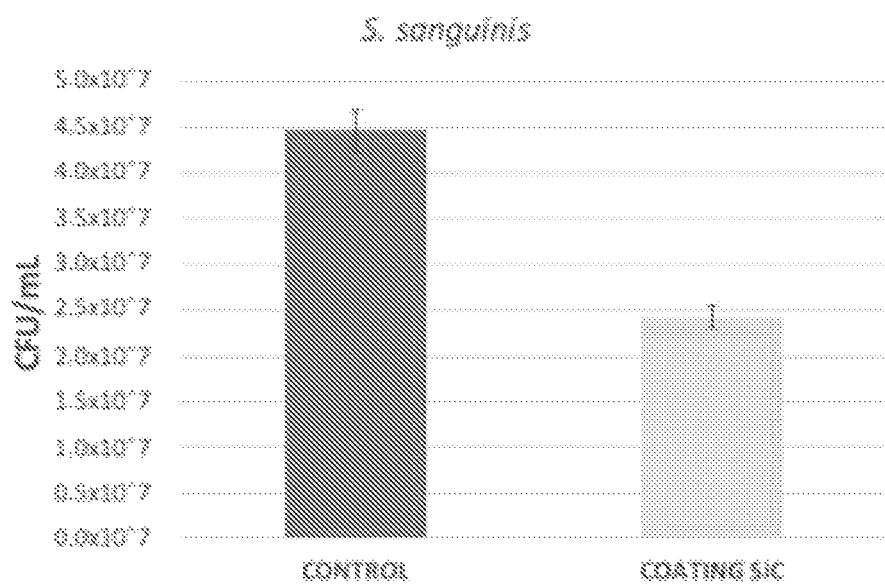

The number of CFU/mL decreased significantly after 24 h of contact with ceramic SiC coating compared to the control group (FIGS. 6A-6B), with p-values of 0.0003 and <0.0001 for *S. sanguinis* and *S. mutans*, respectively. Furthermore, the reductions were similar for *S. sanguinis* and *S. mutans* (p=0.2528).

Example 6: Biocompatibility Testing

Sixteen ceramic specimens of each group were sterilized in an autoclave (121° C., 60 min) and each one was distributed on a sterile 24-well plate. Human Periodontal Ligament Fibroblasts (HPdLF, Lonza) were used to assess biocompatibility. Cells were cultured at 37° C. in a 5% $CO_2$ atmosphere in surface area 175 $cm^2$ polystyrene vented tissue-culture flasks. The cell growth media consisted of Dulbecco's Modified Eagle Medium (DMEM) with 10% fetal bovine serum and 1% penicillin/streptomycin. Cells of passage 3 to 10 were used for subsequent studies. The cells were seeded onto ceramic specimens at a concentration of 20,000 cells/well in 24 well plates and were cultured at 37° C. in 5% $CO_2$.

Cytotoxicity Test

Cell viability was determined using a CellTiter-BlueCell Viability Assay (Promega G808A, Madison, Wis.) according to the manufacturer's instructions. After 24 h, 50 μL of CellTiter-Blue dye were added to ceramic specimens for every 500 μL of culture media and samples were incubated for 6 h at 37° C. and 5% $CO_2$. Sample fluorescence was analyzed using a spectrophotometer (SmartSpec Plus, Bio-Rad) at a wavelength of 600 nm which generated optical density (OD600) values.

Scanning Electron Microscopy

After 24 h of culturing, the cells (HPdLF) adhered to the samples were fixed in a solution of 3% glutaraldehyde, 0.1 M sodium cacodylate, and 0.1 M sucrose for 45 min. Samples were then soaked for 10 min in a buffer solution of 0.1 M sodium cacodylate and 0.1 M sucrose. The samples were then processed in serial ethanol dehydrations (35%, 50%, 70% and 100%) for 10 min each and dehydrated in hexamethyldisilazane (HDMS) and stored in a desiccator until SEM imaging. The samples were sputter-coated with palladium-gold alloy (Polaron SC 7620 Sputter Coater, Quorum Technologies, Newhaven, UK) at a thickness of 10 nm (10-15 mA under a vacuum of 130 mTorr). The SEM was operated at 3 kV, spot 3 to 6 (FEI NOVA 430).

Results

Figure 7:
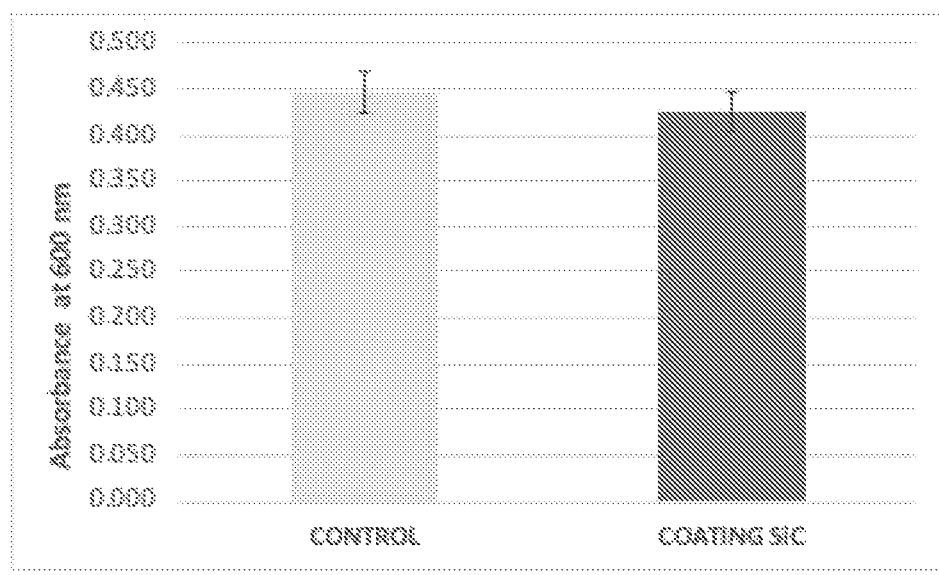
FIG. 7 shows cytotoxicity toward HPdLF cells of non-coated and coated surfaces after 24 h as assessed by a CellTiter-Blue absorbance assay.
Figures 8A, 8B, 8C, 8D, 8E, 8F, 8G, 8H:
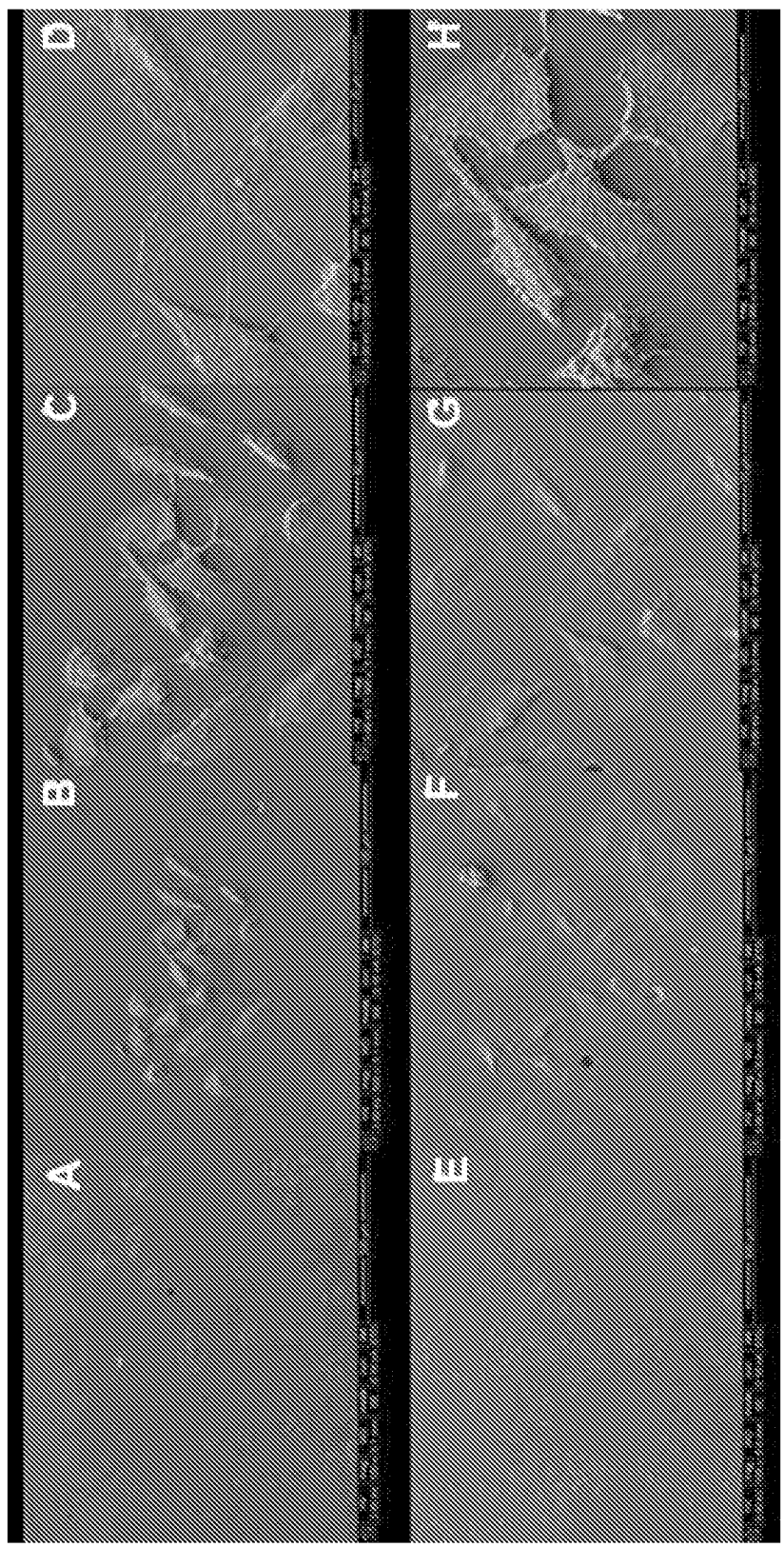
FIGS. 8A-8D show SEM images of adhesion of HPdLF (human periodontal ligament fibroblast) cells on non-coated surfaces after 24 h. Images are from the same field but with different magnifications.
FIGS. 8E-8H show SEM images of adhesion of HPdLF cells on SiC-coated surfaces after 24 h. Images are from the same field but with different magnifications.

In order to determine whether the SiC coating impaired cell proliferation, cytotoxicity was evaluated using the CellTiter-Blue assay. After 24 h of HPdLF cultivation on the samples, no obvious cytotoxicity was observed, with $OD_{600}$ of the cells cultured on SiC coating being comparable to the control group (p=0.3904) (FIG. 7). SEM images show the interaction of cell extensions with the SiC coated and non-coated surfaces, demonstrating that cells adhered and proliferated after 24 h in culture and were distributed on both surfaces (FIGS. 8A-8H).

Example 7: Statistical Analysis

Quantitative data are presented as mean±standard deviation. Statistical differences were compared using one-way ANOVA and Tukey's test (Graph Prism 6.0, Graph Pad Software Inc., La Jolla, Calif., USA). For all analyses, statistical significance was pre-set at α=0.05.

Example 8: Analysis of Failed Dental Implants

Figure 9:
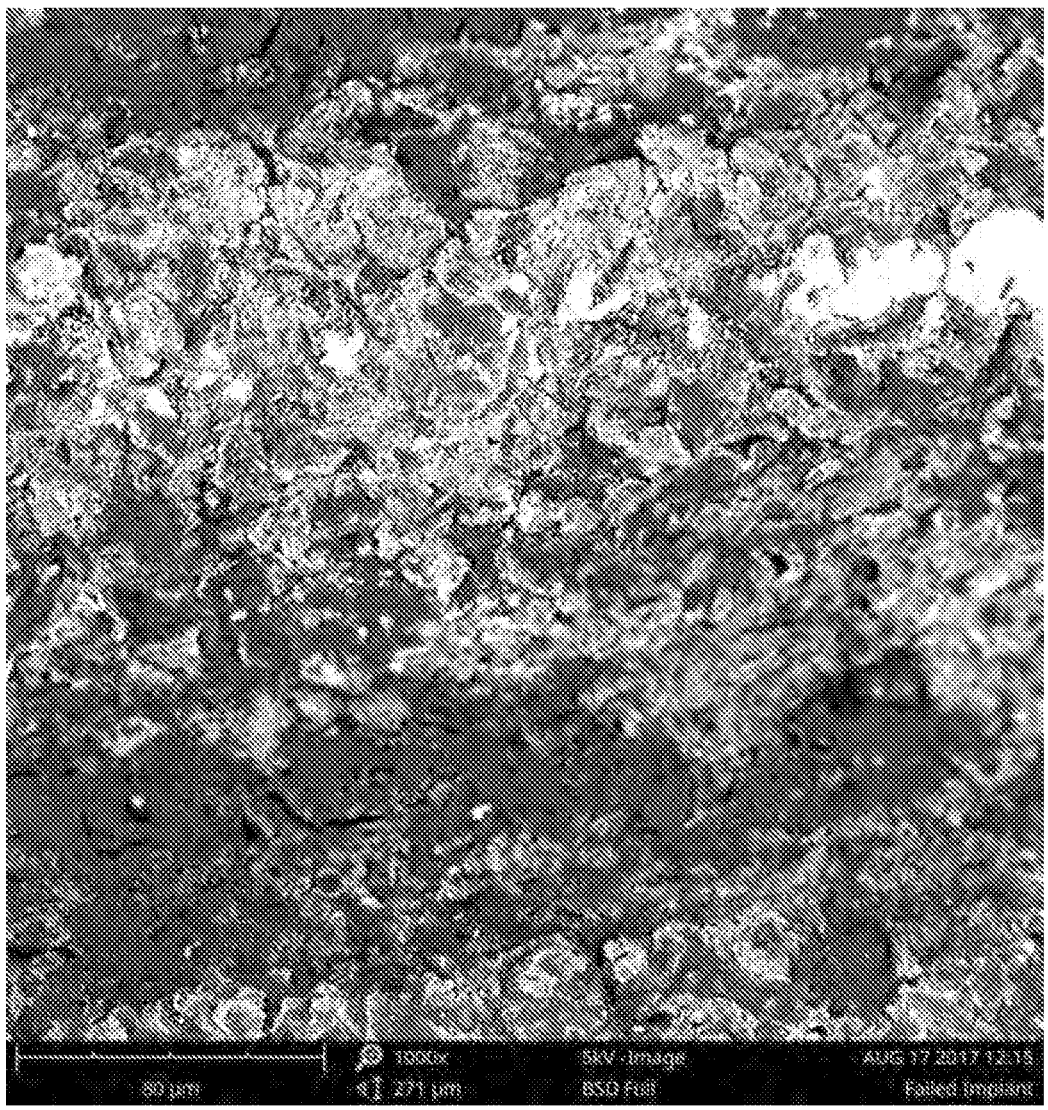
FIG. 9 shows SEM analysis of the surface of a failed implant after five years of service. The surface shows increased surface roughness compared with baseline as well as a decreased Ti concentration on the surface.

In one aspect, energy dispersive X-ray analysis (EDX or EDAX) can be useful for examining the elemental composition of a material. In a further aspect, failed implants display a different elemental composition than reference implants, including having an increased carbon concentration and showing the presence of calcium, which is not seen in reference implants. A comparison of a reference implant and a typical failed implant is shown in Table 2, and an SEM image of a failed implant can be seen in FIG. 9.

TABLE 2

EDX Analysis of Reference and Failed Implants

| Element | Reference Implant | | Failed Implant | |
|---|---|---|---|---|
| | Atomic Percent | Weight Percent | Atomic Percent | Weight Percent |
| Nitrogen | 31.49 | 18.67 | — | — |
| Oxygen | 31.16 | 21.11 | 52.74 | 44.05 |
| Titanium | 26.91 | 54.53 | 12.74 | 31.83 |
| Carbon | 9.12 | 4.63 | 31.85 | 19.97 |
| Fluorine | 1.32 | 1.06 | — | — |
| Phosphorus | — | — | 0.92 | 1.49 |
| Sodium | — | — | 0.84 | 1.01 |
| Calcium | — | — | 0.59 | 1.23 |
| Magnesium | — | — | 0.33 | 0.42 |

Figure 10A:
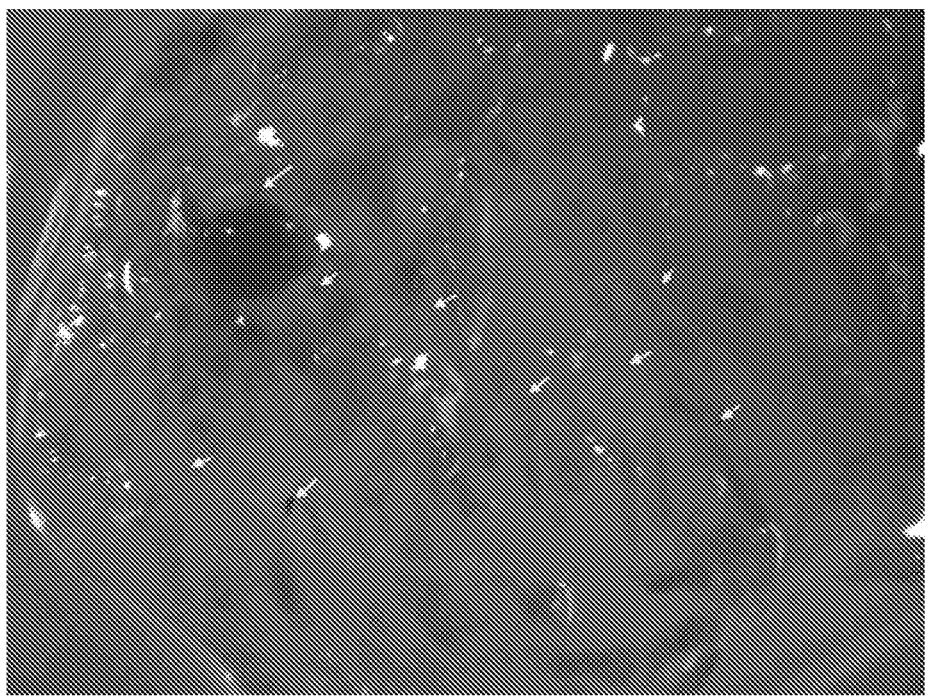
FIG. 10A shows a photograph of titanium from a failed implant embedded in soft tissue (see arrows).
Figure 10B:
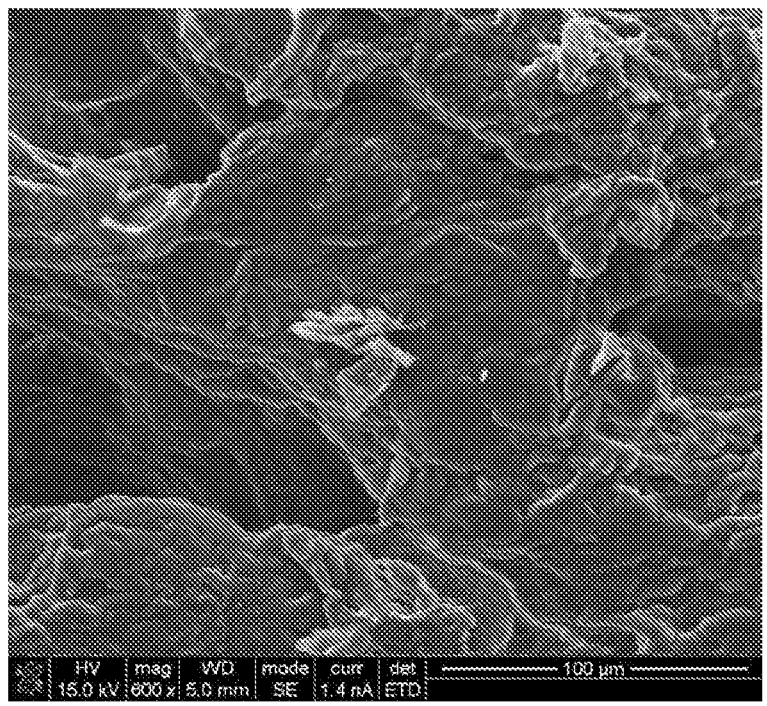
FIG. 10B shows SEM analysis of titanium from a failed implant embedded in soft tissue.
Figure 11A:
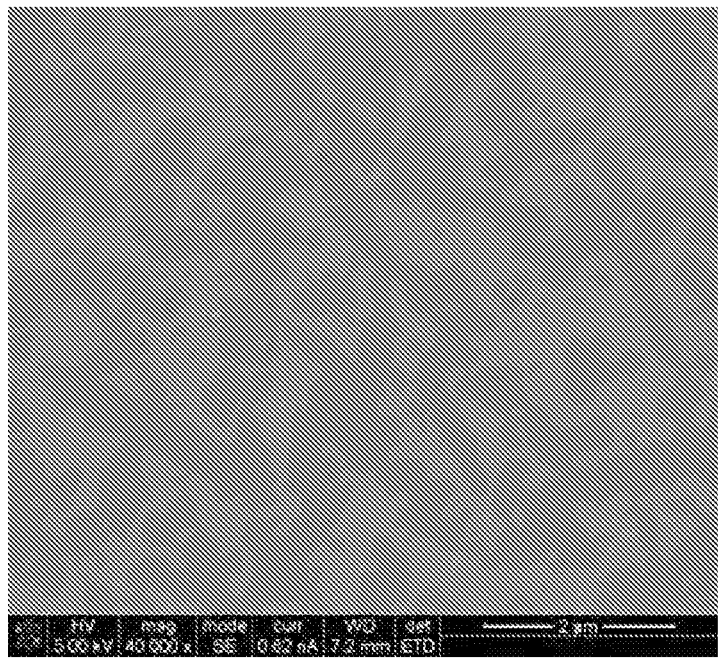
FIGS. 11A-11B are SEM images of bacterial corrosion of ceramic implant surfaces after immersion in biofilm for 40 days, showing that bacteria can degrade even smooth surfaces and indicating a need for antibacterial coatings.
Figure 11B:
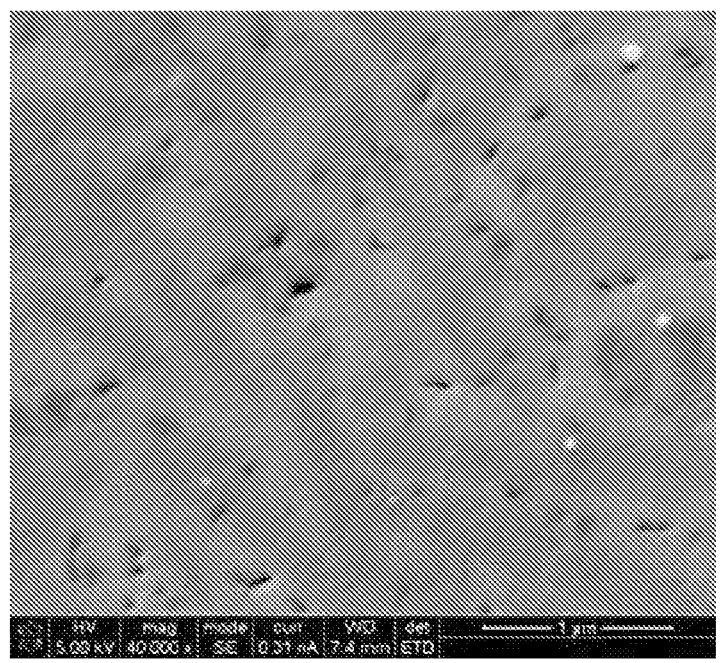
Figure 12A:
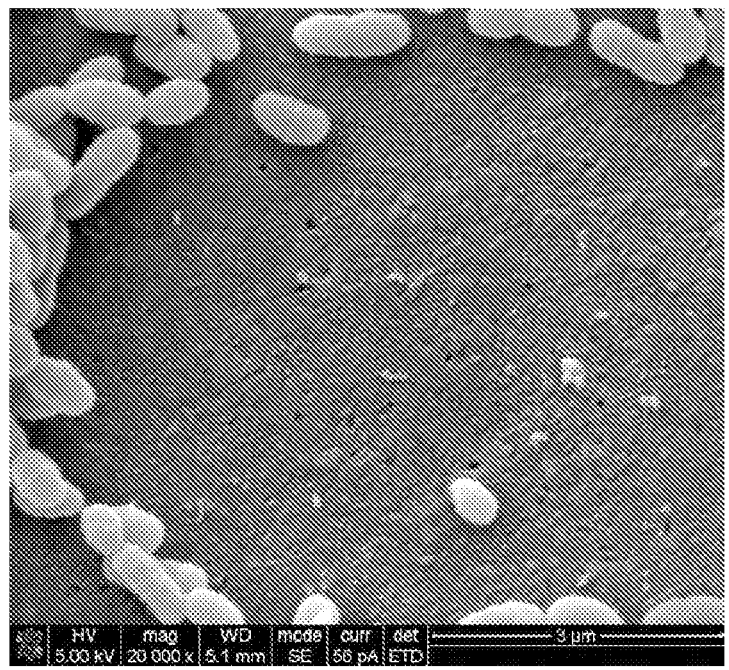
FIGS. 12A-12B show representative SEM images of bacterial corrosion for non-coated and representative coated samples.
Figure 12B:
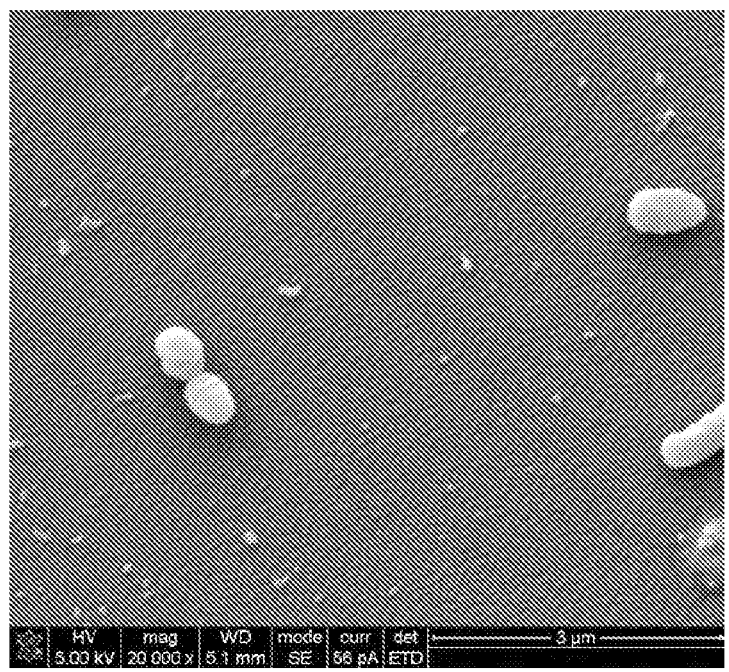

In another aspect, titanium from failed implants can embed in soft tissue (see FIGS. 10A-B) and bacteria from biofilms can further corrode ceramic implant surfaces (see FIGS. 11A-11B and FIGS. 12A-12B).

Example 9: Anti-Corrosive Properties of the Coatings

SiC Coatings on Ceramic

Figure 13:
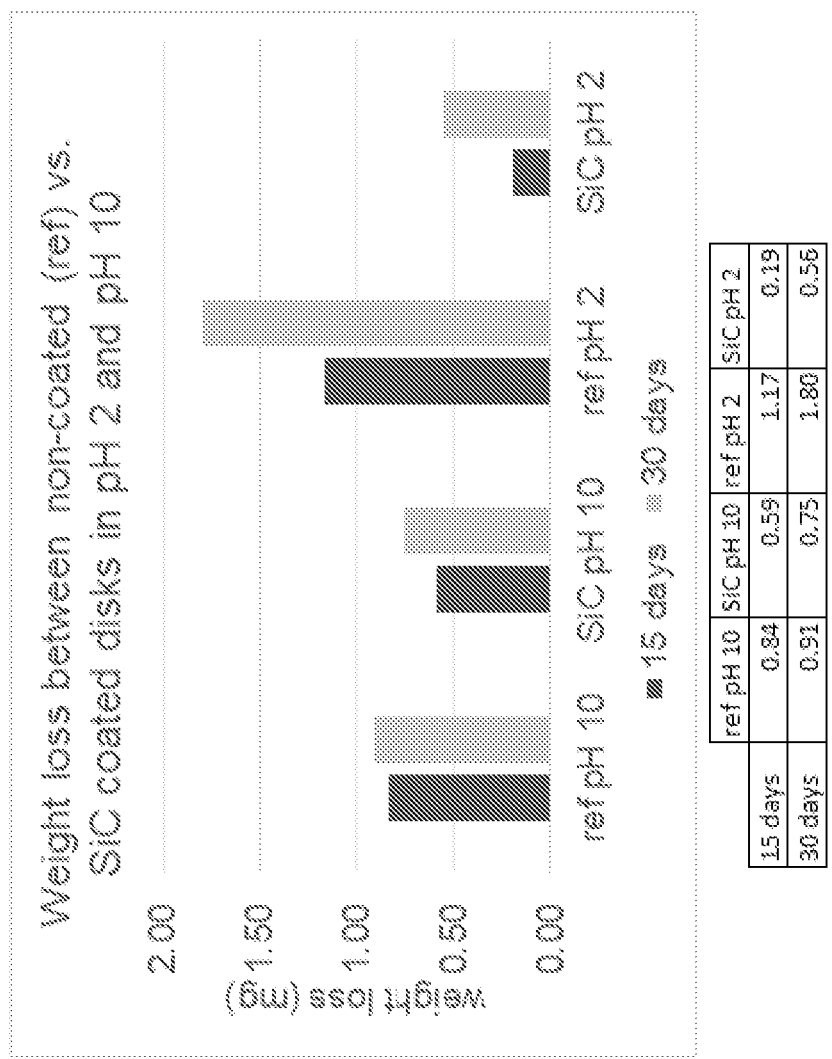
FIG. 13 shows weight loss in basic (pH 10) and acidic (pH 2) solutions for non-coated (ref) and SiC-coated ceramic disks after 15 and 30 days in an 80° C. water bath with shaking at 50 oscillations per minute.
Figures 14A, 14B, 14C, 14D, 14E, 14F:
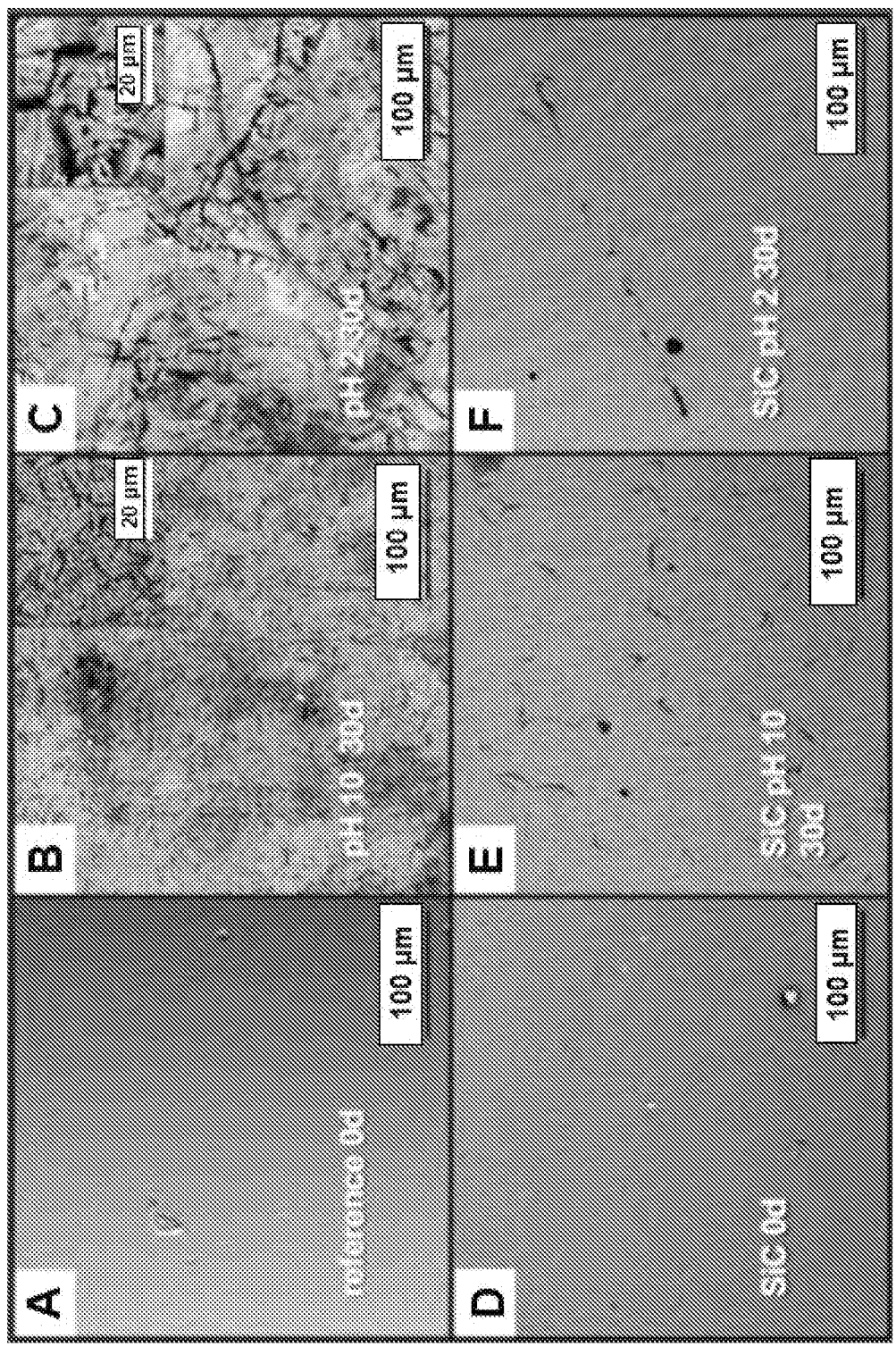
FIGS. 14A-14F shows representative SEM images of non-coated and representative coated samples as follows.

Non-coated (ref) and SiC coated discs were exposed to solutions having pH 10 and pH 2 for 15 and 30 days, respectively. SiC-coated disks showed somewhat less weight loss at pH 10 and significantly less weight loss at pH 2 compared to reference samples at both 15 and 30 days (see FIG. 13). Samples were dried in a 100° C. oven, cooled to room temperature and stored in a desiccator until weighing. Following weighing, samples were immersed in an 80° C. water bath shaken at 50 oscillations per minute for the listed time periods, after which the weighing procedure was repeated to determine weight loss. SEM images of disks exposed to different pH conditions are shown in FIGS. 14A-14F.

Quaternized and Non-Quaternized Coatings on Titanium Disks

To study the bacterial corrosion of the coated and non-coated titanium disks, monomicrobial reference strains (ATCC—American Type Culture Collection) of *Porphyromonas gingivalis* (ATCC 33277), *Streptococcus salivarius* (ATCC BAA-1024), *Streptococcus sanguinis* (ATCC BAA-1455) and *Streptococcus mutans* (ATCC 35688) were used. The strains were grown in Falcon tubes with brain heart infusion broth (BHI—Himedia) for 24 and 48 hours at 37° C. After the growth, each microbial suspension was centrifuged at 4700 rpm for 10 min (MPW-350) to separate the supernatant and microbial suspension. The centrifuge process was performed twice to minimize the quantity of debris. After separation, the microbial suspension adjusted to $10^7$ CFU/mL.

Coated and non-coated titanium disks of each group were sterilized in autoclave (121° C., 60 min), and each one was distributed on a sterile 12-well plate. For all samples, 1 mL of polymicrobial suspension was added to each well containing a coated or non-coated Ti disk and cultivated for 30 days.

ICP-MS Analysis

Culture media was collected every 2 days for 30 days of culturing, and ICP-MS (inductively coupled plasma-mass spectrometry) testing was performed to determine the amount of titanium in the supernatant.

Samples were vortexed immediately prior to aliquoting into 4 mL duplicates. Accurate weights of the aliquots were recorded since their specific gravity is approximately equal to that of water. One aliquot of each sample was fortified with 50 ng of a Ti internal standard. One mL of 70% nitric acid (Fisher Scientific, Hampton, N.H.) and 0.5 mL 30% certified ACS grade hydrogen peroxide (Fisher Scientific) were added to the samples, which were then heated to 100° C. on a dust-free hotplate for 1.5 hours. After digestion and cooling, the samples were brought to 15 mL by weight with ultrapure water, again accurately recording dilution weight. Procedural blanks were also tested alongside samples to ensure purity of the reagents. Testing for Ti was accomplished using an Agilent 7900 ICP-MS (Santa Clara, Calif.) with in-line internal standard addition and utilizing He gas mode, which reduces polyatomic interferences. The Ti isotope to be monitored is 48, the most abundant of naturally occurring Ti isotopes. A set of Ti calibrators with a range 0-10,000 ppb was also be tested to quantitate the samples' Ti concentrations.

Uncoated Ti disks in contact with bacteria for 30 days released high concentrations of Ti (34.46 ppb) compared with all groups ($p<0.05$). Ti disks coated with SiC released the lowest amount of Ti with 0.54 ppb for SiC and 3.6 ppb for qSiC ($p<0.05$) (FIG. 2). TiN (9.57 ppb) and qTiN (11.02 ppb) coated disks presented similar Ti release values.

Weight Measurements

The disks were weighed before and after the 30-day bacteria corrosion experiment. Disks were weighed using an analytical balance (AS 220.R2 Analytical Balance, Radwag, Poland). Each disk was weighed three times, the average values were calculated for the weight for each disk. After the bacteria corrosion experiment, the disks were cleaned with Triton X-100 and distilled water and dried before the weighing. Weight measurements were performed as a verifying step to see if the 30 days immersion in bacteria led to an excessive loss in sample weight (implant weight).

The initial and final weights of coated and non-coated samples were similar in all samples ($p>0.05$). An obvious difference between the initial and final weight was not observed for any sample, showing no high degradation on Ti disks after 30 days of cultivation with biofilm (FIG. 3).

Scanning Electron Microscopy

Non-coated and coated disks were observed using scanning electron microscopy with a MAICE system (JEOL JSM-6400 Scanning Electron Microscope, JEOL LTD, Tokyo, Japan) to identify surface roughness before and after cultivation with a biofilm. Coated (TiN, qTiN, SiC, qSiC) and non-coated disks were incubated for 30 days. The polymicrobial biofilm adhered to the samples was removed by placing the disks inside a Falcon tube with 2 mL of Triton X-100 and vortexing for 2 min. The disks were then washed 3× with 2 mL of distilled water. The SEM was operated at 5 kV, spot 3 to 6 (JEOL JSM-6400) and the images were recorded.

FIGS. 21A-21J demonstrate the change in surface roughness of Ti reference and Ti coated disks before and after bacterial inoculation. The reference disk (FIG. 1F) showed pitting and surface breakdown, while these were not evident with the coated samples (FIGS. 1G-J).

Atomic Force Microscopy

Topographies of Ti, TiN, qTiN, SiC, and qSiC disks were verified using an atomic force microscopy system (Bruker/Veeco/Digital Instruments NanoScope V). The AFM was operated in tapping mode using a silicon AFM probe (RTESP-300, Bruker), with a radius of less than 10 nm and resonance frequency among 200 and 400 kHz.

The quantitative data are shown as the means±standard deviations. Statistical differences were calculated using one-way ANOVA and Tukey's test (GraphPad Software Inc.), with a p-value of ≤0.05 being considered statistically significant.

Figure 24:
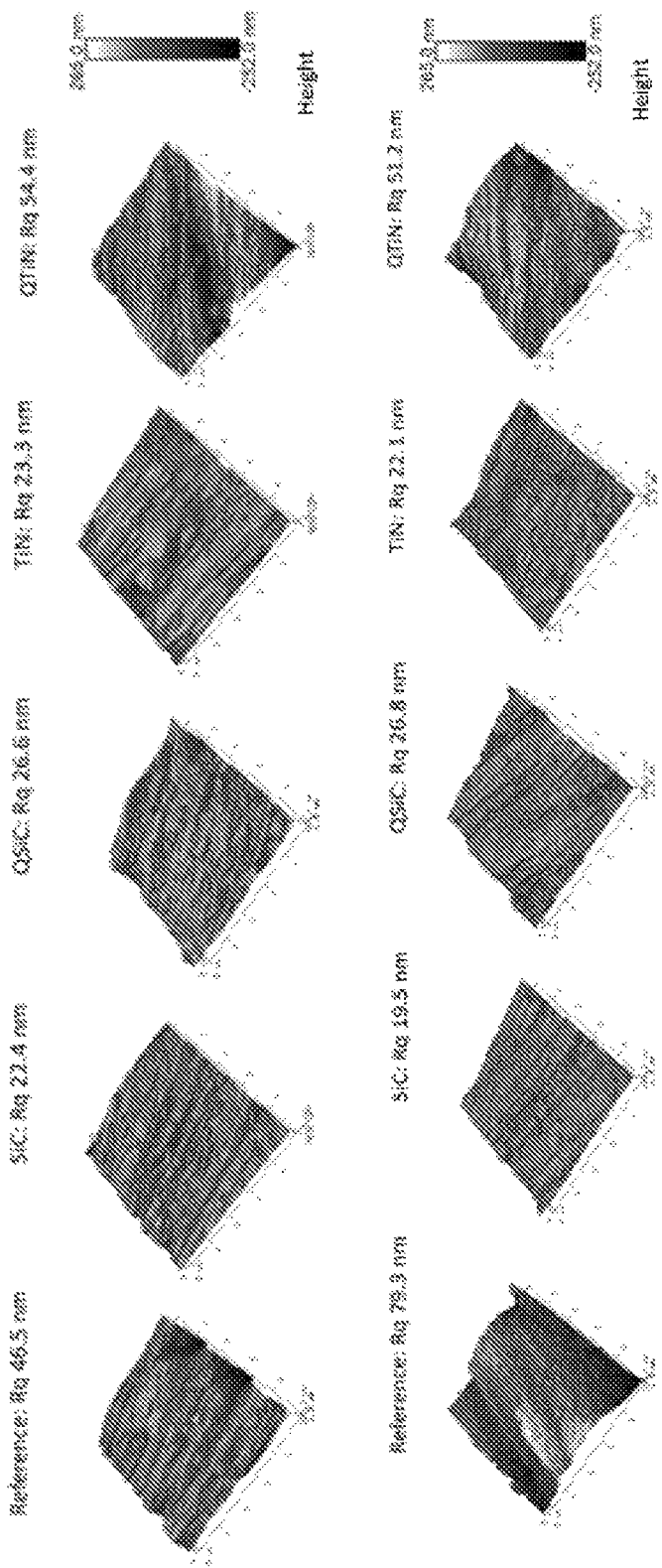
FIG. 24 shows AFM images of surface topography of coated and non-coated Ti disks with amplifications of 10 μm. Samples include a non-coated (reference) sample as well as disks coated with TiN, qTiN, SiC, and qSiC. The top row represents samples prior to cultivation with bacteria, while the bottom row represents samples after 30 days in contact with bacterial cultures as described elsewhere herein.
Figure 25:
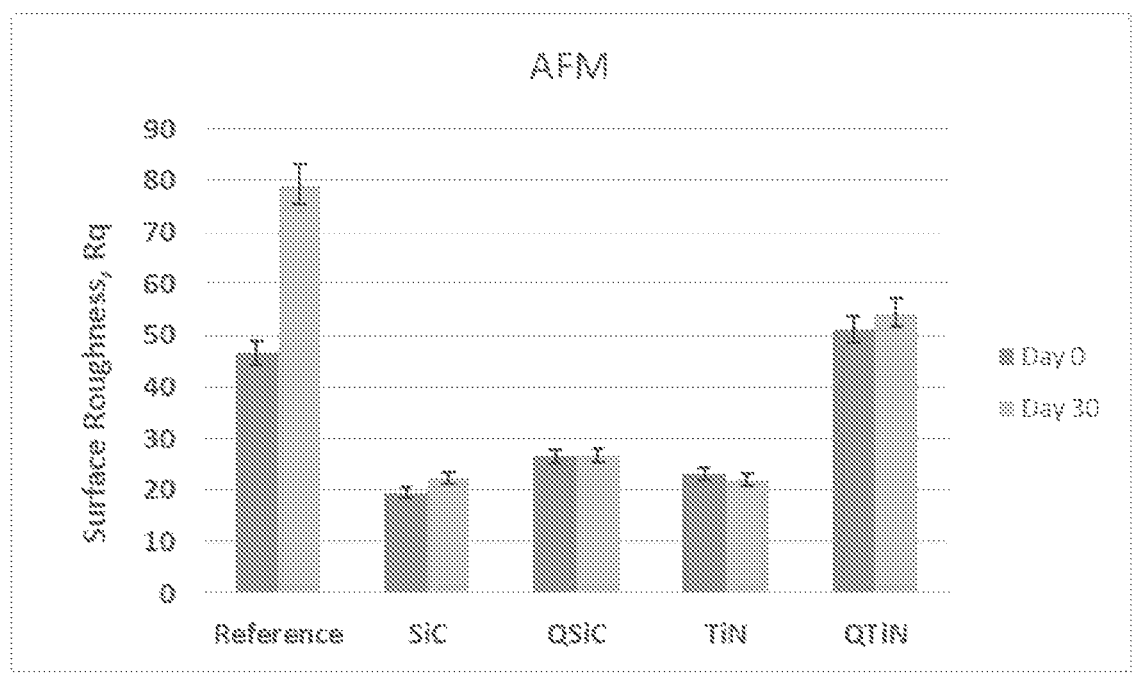
FIG. 25 shows roughness values as measured by AFM in non-coated ("Reference") and coated (TiN, qTiN, SiC, and qSiC) disks initially ("Day 0") and after 30 days in bacterial culture. Error bars represent standard deviation.

The roughness of non-coated and coated disks was measured before and after 30 days in contact with a biofilm (FIG. 24). Non-coated Ti disks presented similar surface roughness (Rq) as qTiN on Day 0, however it was higher on Day 30.

After 30 days in cultivation with a biofilm, we observed that the Rq values were higher only for non-coated Ti disks (p<0.05) (FIG. 24, top row). All coated disks presented Rq values similar initially (Day 0) and after 30 days of cultivation (p>0.05) (FIG. 24, bottom row). The highest Rq values were 51.2 mm and 54.4 mm for qTiN for day 0 and day 30, respectively.

The spatial parameters were reported in the present study (Table 3), the autocorrelation length (Sal) and the texture aspect ratio (Str). The autocorrelation length was the fastest decay in the perpendicular direction to the texture and the texture aspect ratio was represented as a ratio of the fastest and slowest decay. The non-coated disks (reference) and coated disks seemed to have an anisotropic texture in general (TiN seemed to be a ransom structure, the Str is above 0.5).

The SEM images showed that the non-coated (reference) disk is rough, and the coating was able to planarize the disks conformally. The image roughness demonstrated less roughness (image Rq) from the coating compared with the non-coated sample. The AFM and SEM data showed a similar trend. Usually, the rough surface showed more than 1% Sdr. The Sdr was 4.44% and 4.25% for non-coated and QTiN coated disk, while the Sdr decreased for the other coatings. After bacterial incubation, the non-coated showed higher surface roughness (image Rq) and the higher Sdr, whereas the rest of the samples showed similar results.

TABLE 3

Spatial Parameters Determined by SEM and/or AFM for Non-Coated (Reference) and Coated Discs Initially (Day 0) and after 30 Days of Cultivation with Bacteria

| | Height | Spatial | | Hybrid |
|---|---|---|---|---|
| No Bacteria (Day 0) | Sq (=Image Rq) | Sal (µm) | Str | Sdr (%) |
| Reference | 46.5 | 0.676 | 0.297 | 4.44 |
| SiC | 22.4 | 0.285 | 0.272 | 2.41 |
| QSiC | 26.6 | 0.428 | 0.463 | 1.95 |
| TiN | 23.3 | 0.535 | 0.616 | 1.73 |
| QTiN | 54.4 | 0.549 | 0.203 | 4.25 |

| | Height | Spatial | | Hybrid |
|---|---|---|---|---|
| Bacteria (Day 30) | Sq (=Image Rq) | Sal (µm) | Str | Sdr (%) |
| Reference | 79.3 | 0.765 | 0.207 | 6.52 |
| SiC | 19.5 | 0.485 | 0.371 | 2.89 |
| QSiC | 26.8 | 0.511 | 0.157 | 2.77 |
| TiN | 22.1 | 0.570 | 0.781 | 3.34 |
| QTiN | 51.2 | 0.754 | 0.363 | 2.7 |

Example 10: Preparation of Charged TiN Implant Surfaces for Dental Implants

Titanium

The starting substrates were 1 inch by 1 inch cover glasses. Substrates were cleaned with acetone, isopropanol (IPA) and dilute HCl (10% in deionized (DI) water). To simulate a Ti implant, 100 nm of high purity Ti (0.9999) was deposited on the cover glass surface by electron beam evaporation at a pressure of $8\times10^{-7}$ Torr. Prior to biofilm growth, the Ti samples were rinsed with the following solvent sequence: acetone, IPA, and DI water. Upon exposure to the ambient atmosphere, low quality native oxides are present on all Ti surfaces. The native oxides were removed by sonicating the samples in 1:10 HCl:DI water, then treating with hydrogen peroxide at 60° C. to grow a high-quality oxide layer. Contact angle was used to verify consistent samples surfaces from batch to batch.

Titanium Nitride 1 inch by 1 inch cover glasses were also used for preparing for TiN substrates, and were also cleaned with acetone, IPA and dilute HCl. 1000 Å titanium was first deposited by rf-magnetron sputtering at a deposition pressure of 5 mTorr in Ar atmosphere on cover glasses. The Ti base layer was employed to simulate a Ti implant being plasma spray coated with titanium nitride. Without removing the sample from the chamber, 500 Å of TiN was subsequently deposited by rf-magnetron sputtering with a TiN target at room temperature in a pure Ar atmosphere. The platen for holding the samples was biased at 30-40 V to improve uniformity and stoichiometry of deposited TiN layer. Prior to biofilm growth the TiN samples were rinsed with acetone, IPA, and DI water and sonicated in 1:10 of HCl: DI water. Contact angle was used to verify consistent samples surfaces from batch to batch.

Quaternized Titanium Nitride

Quaternized TiN substrates were prepared by converting nitrogen atoms on TiN surface into quaternary nitrogen by submerging the TiN substrates in an acetonitrile and allyl bromide solution for 1 hour to quaternize the surface. After quaternization, an IPA and DI water rinse was used to remove any excess solvent and reagent. Contact angle measurements were used to verify consistent samples surfaces from batch to batch.

Biofilm Incubation and Testing

All bacteria work used sterilized materials and was performed under flame to prevent any cross contamination from outside sources. Samples were autoclaved at 125° C. for 20 minutes immediately prior to growth and were kept in sealed containers until removed.

On the day of testing, a paper point was used to extract subgingival bacteria between the lower last premolar and first molar from a patient. The paper point was placed in Ringer solution to suspend and preserve the bacteria. To remove the bacteria from the paper point, the sample was vortexed and sonicated, then vortexed again prior to any removal of bacteria containing solution from the container.

Each sample to be tested for bacteria growth was placed in an individual sterile container. Bacteria solution was micropipetted on to the surface to form film thicknesses (z-height) of 75, 100 and 125 μm. The samples were incubated in a Bactron 300 anaerobic chamber in a dark box for 4 hours. This time period provided significant quantifiable differences in bacteria growth between the samples. Post-incubation, the bacteria solution was removed from the sample surface by sonicating and vortexing in fresh Ringer solution. The resulting Ringer solution was further diluted and plated on Tryptic Soy Agar and allowed to grow under anaerobic conditions for 48 hours. Subsequently, the plates were removed and colony forming units counted to evaluate antibacterial efficiency of the quaternized sample as compared to reference titanium and titanium nitride samples.

Confirmation of Reaction

To confirm a successful Menshutkin surface reaction of the TiN implant with the reagent, Sessile contact angle measurement was used (Table 4). The TiN sample was very hydrophilic after deposition and cleaning, due to the high ability for hydrogen bonding of the water droplet to the nitrogen rich surface. The titanium sample after treatment with hydrogen peroxide is expected to be very hydrophilic due to the high quantity of Ti—OH and Ti=O bonds present. The cleaning treatments that were developed for each surface was in part to ensure that a highly reproducible surface could be created and give the low variance in contact angle that is reported.

TABLE 4

Contact Angle Measurement of Quaternized Surfaces

| Sample | Contact Angle (°) |
|---|---|
| Titanium after $H_2O_2$ clean | 12 ± 2 |
| TiN after clean | <6 |
| TiN in solvent 120 min (no reagent) | 16 ± 2 |
| TiN Quaternization 30 minutes | 67 ± 1 |
| TiN Quaternization 60 minutes | 72 ± 3 |
| TiN Quaternization 120 minutes | 71 ± 2 |

With the quaternized TiN surface, prior to measurement, the contact angle is difficult to predict as the surface does become charged with the quaternized nitrogen lending to potential hydrophilicity; however, the carbon chain from the allyl group extends from the surface leading to potential hydrophobicity. A reference TiN sample was soaked in the solvent to ensure any changes related to the acetonitrile could be accounted for and not be mistaken for a surface reaction. This reaction produced a contact angle of ~72°, distinct from all other disk types and the control in solvent (22°). Menshutkin reactions are known to progress very rapidly; this reaction saturated within an hour. Of note, the allylic halide will react more quickly with higher substituted amines due to the lower enthalpy of formation. Thus, this reaction is well suited for formation of quaternary ammonium salts and is difficult to stop at secondary or tertiary products.

To further confirm and identify change in surface chemistry XPS was performed. XPS surface analysis was employed to further confirm and identify changes in surface chemistry of quaternized TiN surface. Wide range analyses were acquired from the surface of the TiN and quaternized TiN substrates and Ti, O, N and C were the only elements identified on these two samples; indicating the general surface chemistry of TiN and quaternized TiN samples were identical. Therefore, a detailed peak analysis was necessary for confirmation of the surface reaction. High resolution XPS spectra of the N 1s regions acquired at 0 and 50° angles with respect to the normal for the TiN and quaternized TiN surfaces. The main N peak corresponded to Ti—N bonds located at 396.75 eV and an N satellite peak was found at 398.48 eV. The shoulder peak of N for Ti—N at 394.5 eV resulted from N on N—Ti—O. The XPS peak for quaternized nitrogen bound to ethyl groups (—$CH_2CH_3$), $N^+$ was 399.75 eV. As compared to the 0° spectra, surface effects were more pronounced for the spectra taken 50° tilted and the penetration depth of the x-ray source was greatly reduced. For the N spectra of TiN substrate, the peak corresponding to the N of N—Ti—O was more pronounced due to the oxide presence on the TiN surface. For the N 1s spectra of the quaternized nitrogen, this effect was evident in the increased relative intensity of the quaternized nitrogen peak at 399.75 eV to the TiN peak at 396.5 eV, at 50°, indicating the $N^+$ atoms situated on the surface of quaternized TiN.

Example 11: Impact of Quaternized TiN Surface on Biofilm Growth

Figure 15A:
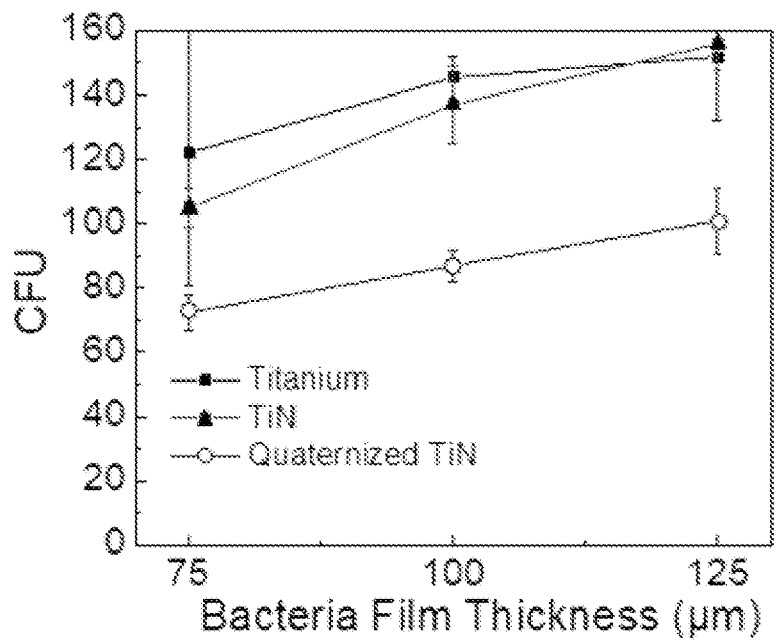
FIGS. 15A-15B show representative data for biofilm coverage by *P. gingivalis* after 4 hours of culture on non-coated (Ti control) and coated (quaternized SiC, or qSiC) surfaces.
Figure 15B:
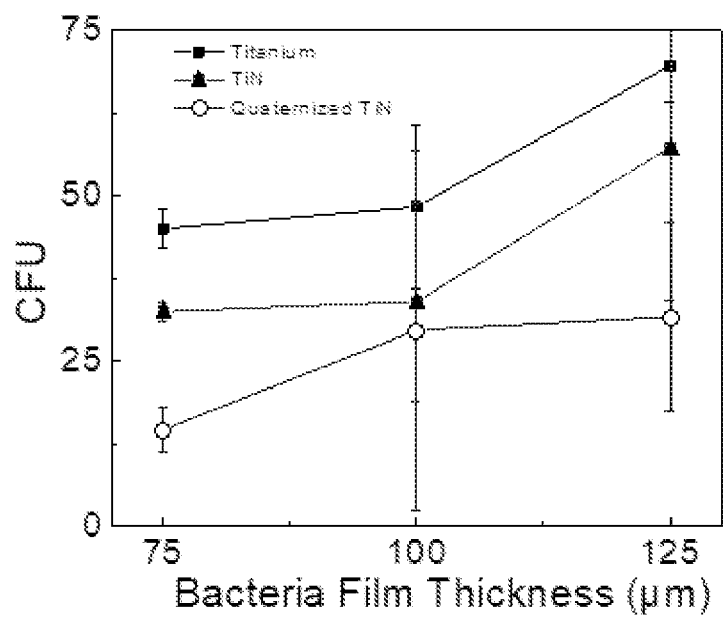

FIGS. 15A-B show colony forming units (CFU) for different thicknesses of bacterial solution kept between cover glass slips and Ti, TiN or quaternized TiN. The proposed mechanism of quaternized nitrogen is interaction with cell walls and destruction of cytoplasmic membranes, leading to the leakage of intracellular components and consequent cell death. The quaternized surfaces outperformed the both the traditional TiN and titanium implants significantly within the short four-hour testing period for bacteria film thickness of 75 μm. Even with bacteria films that are 125 μm thick, the quaternized surfaces still significantly outperformed the other two substrates indicating that the surface has the ability to neutralize bacteria many microns away. The surface must have this ability to affect bacteria at a distance, as the implant will be surrounded initially by saliva and soft tissue until full osseointegration is complete. Additionally, failure of an implant would be induced by an infection beginning near the soft tissue which would propagate towards the base of the implant.

Example 12: Quaternization of SiC Coatings

Quaternized SiC (qSiC) substrates were prepared by adding nitrogen atoms to the SiC surface coatings, which was accomplished by treating the SiC surface with $NH_3$ plasma in a plasma-enhanced chemical vapor deposition (PECVD) system using 400 W at 300° C., 100 sccm $NH_3$ at 800 mTorr. The surface was then rinsed using acetone, isopropyl alcohol (IPA), and DI water and blown dry with $N_2$. The treated surface nitrogen atoms were then converted into quaternary nitrogen by submerging the SiC-coated substrates in an acetonitrile and allyl bromide solution for 1 hour to quaternize the surface. After quaternization, an IPA and DI water rinse was used to remove any excess solvent and reagent. Contact angle measurements were used to verify consistent sample surfaces among batches.

Example 13: Growth of *Porphyromonas gingivalis* on qSiC Coated Surfaces

Figure 16:
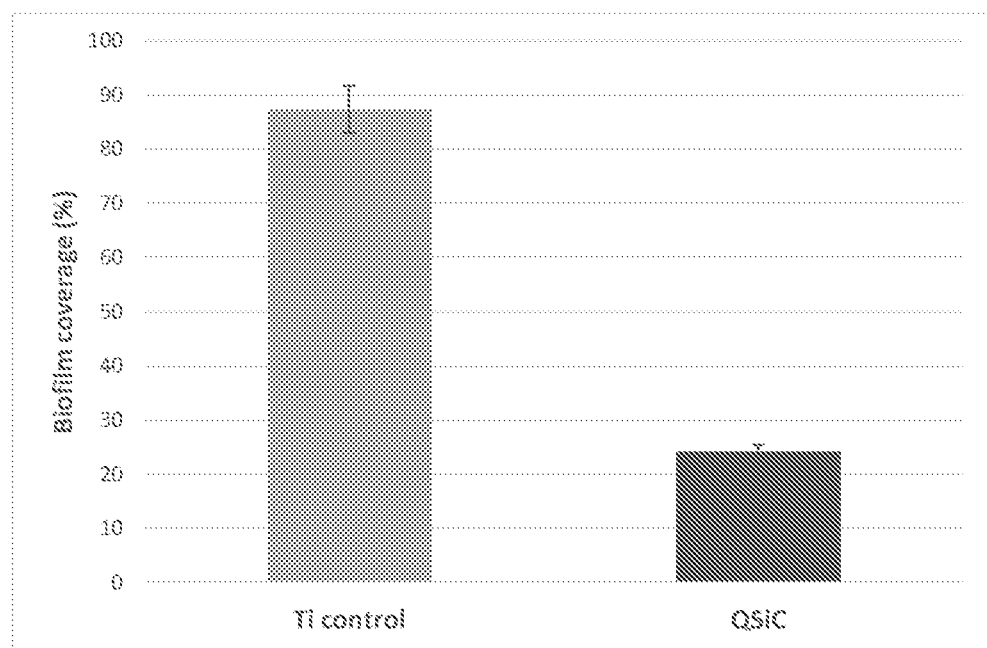
FIG. 16 shows live coverage of *P. gingivalis* after 4 hours of culture on a non-coated (Ti control) and coated surface (qSiC).
Figures 17A, 17B, 17C, 17D, 17E, 17F:
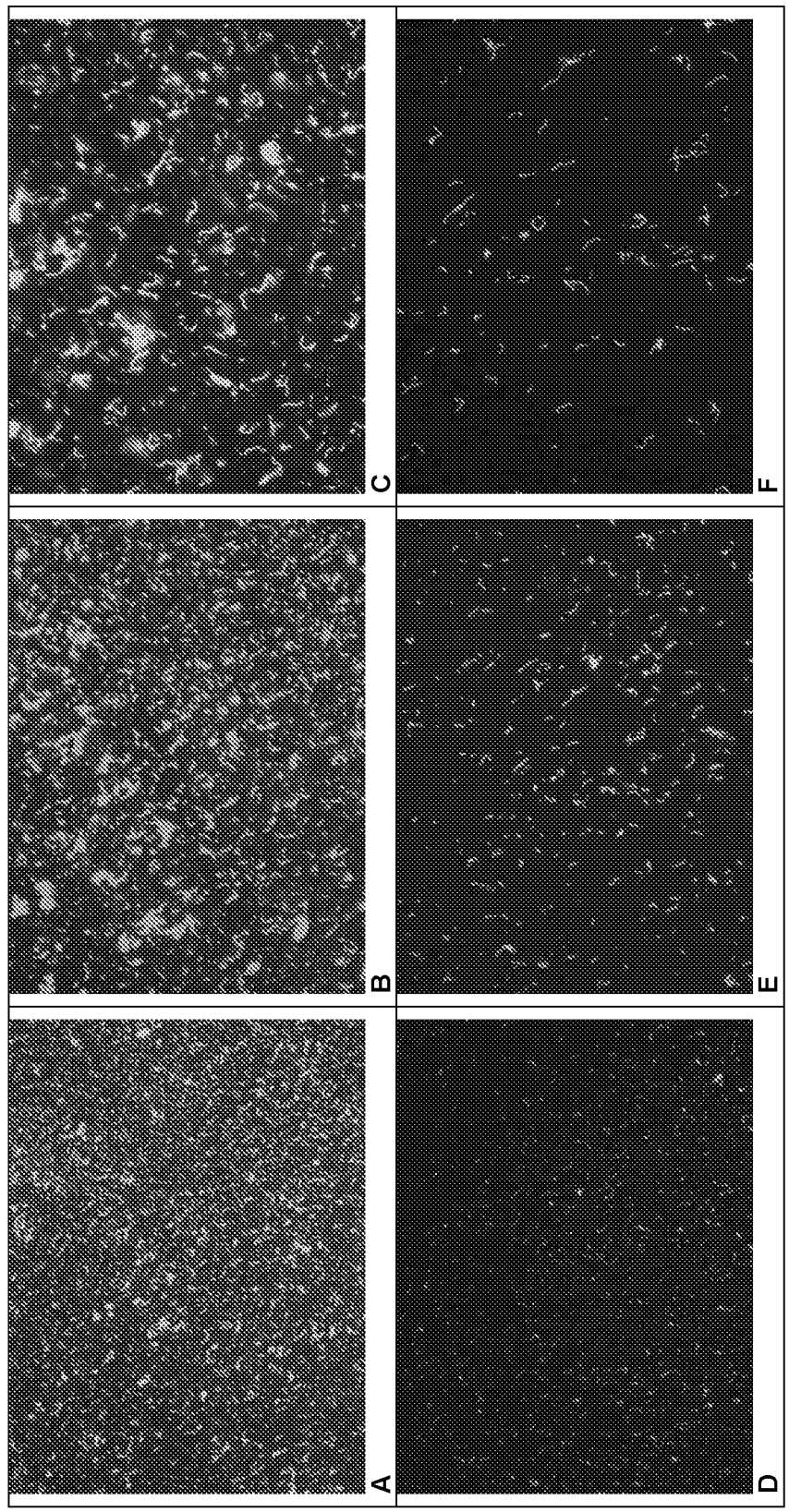
FIGS. 17A-17F show live fluorescence images of *P. gingivalis* cultured for 4 hours on a non-coated Ti surface at different magnifications (FIGS. 17A-17C) and a qSiC surface at different magnifications (FIGS. 17D-17F). Cultures were stained with SYTO® 0, which dyes living bacteria green.
Figures 18A, 18B, 18C, 18D, 18E, 18F:
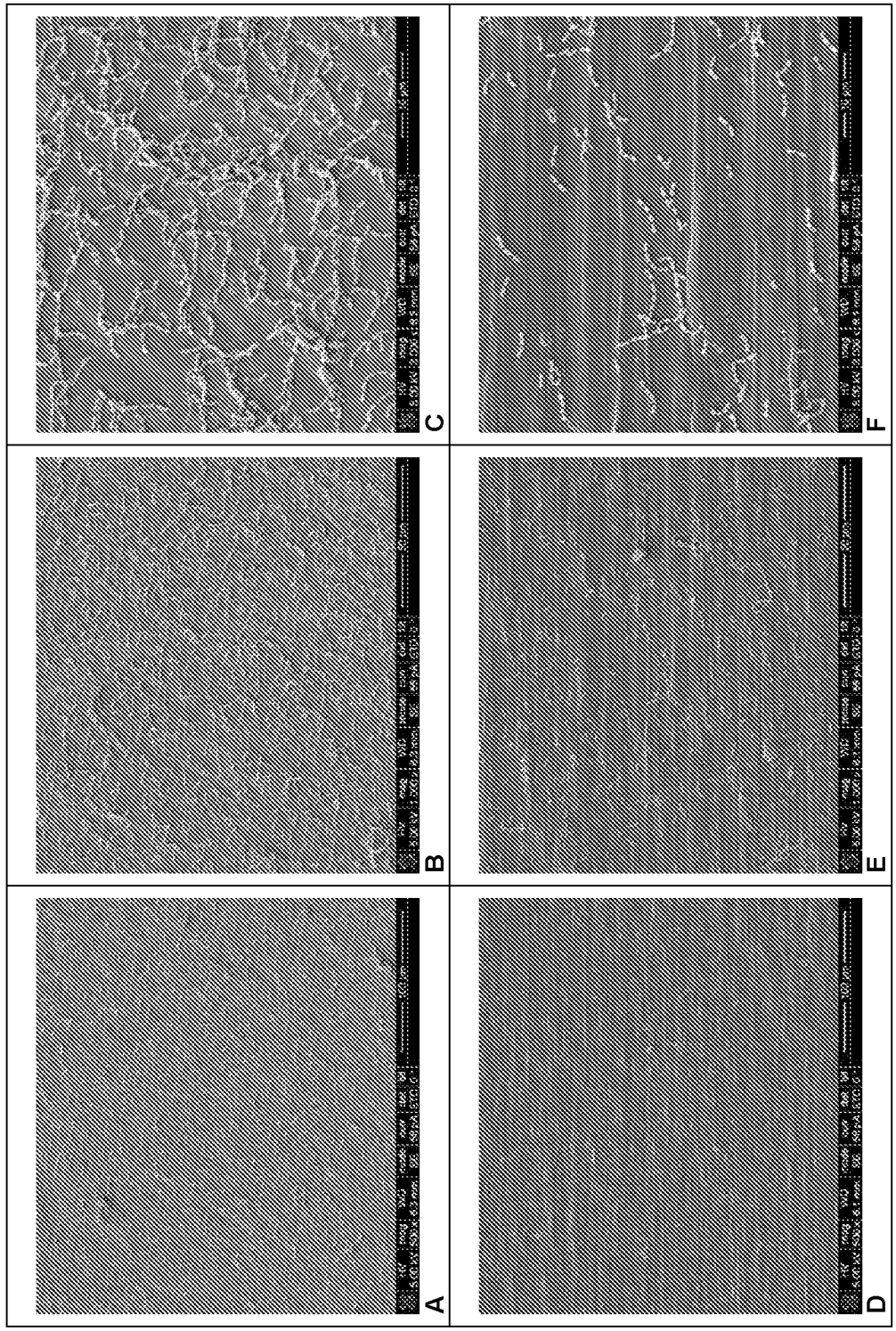
FIGS. 18A-18F show SEM images of adhesion of *P. gingivalis* after 24 hours of cultivation on a non-coated Ti surface at different magnifications (FIGS. 18A-18C) and a qSiC surface at different magnifications (FIGS. 18D-18F).

*Porphyromonas gingivalis* cultures were seeded on a control device with titanium coating and on a titanium device coated with quaternized SiC. After 4 h, the coverage by monomicrobial biofilm was less on the titanium coating with qSiC than on the untreated control. Samples that were coated with qSiC showed a biofilm coverage of 24.24% whereas reference samples that were uncoated showed a significantly higher biofilm coverage of 87.25% (p<0.0001) (FIG. 16). The fluorescence images in FIGS. 17A-17F demonstrate higher biofilm formation on the control group than the coated group.

SEM images confirm the results from the live assays, showing a reduction in the number of adherent bacteria on the coated group for *P. gingivalis* after 24 h of culture (FIGS. 18A-18F).

Example 14: Biocompatibility of qSiC Coatings

Figure 19:
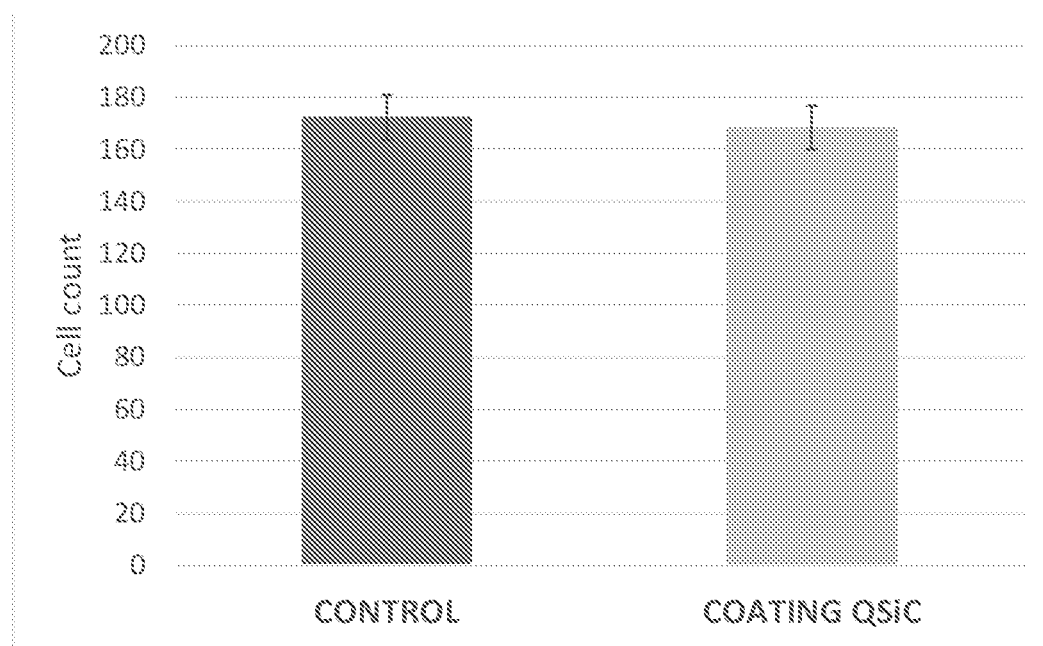
FIG. 19 shows cell proliferation after 24 hours of culture on non-coated and coated (qSiC) surfaces.
Figures 20A, 20B, 20C, 20D, 20E, 20F:
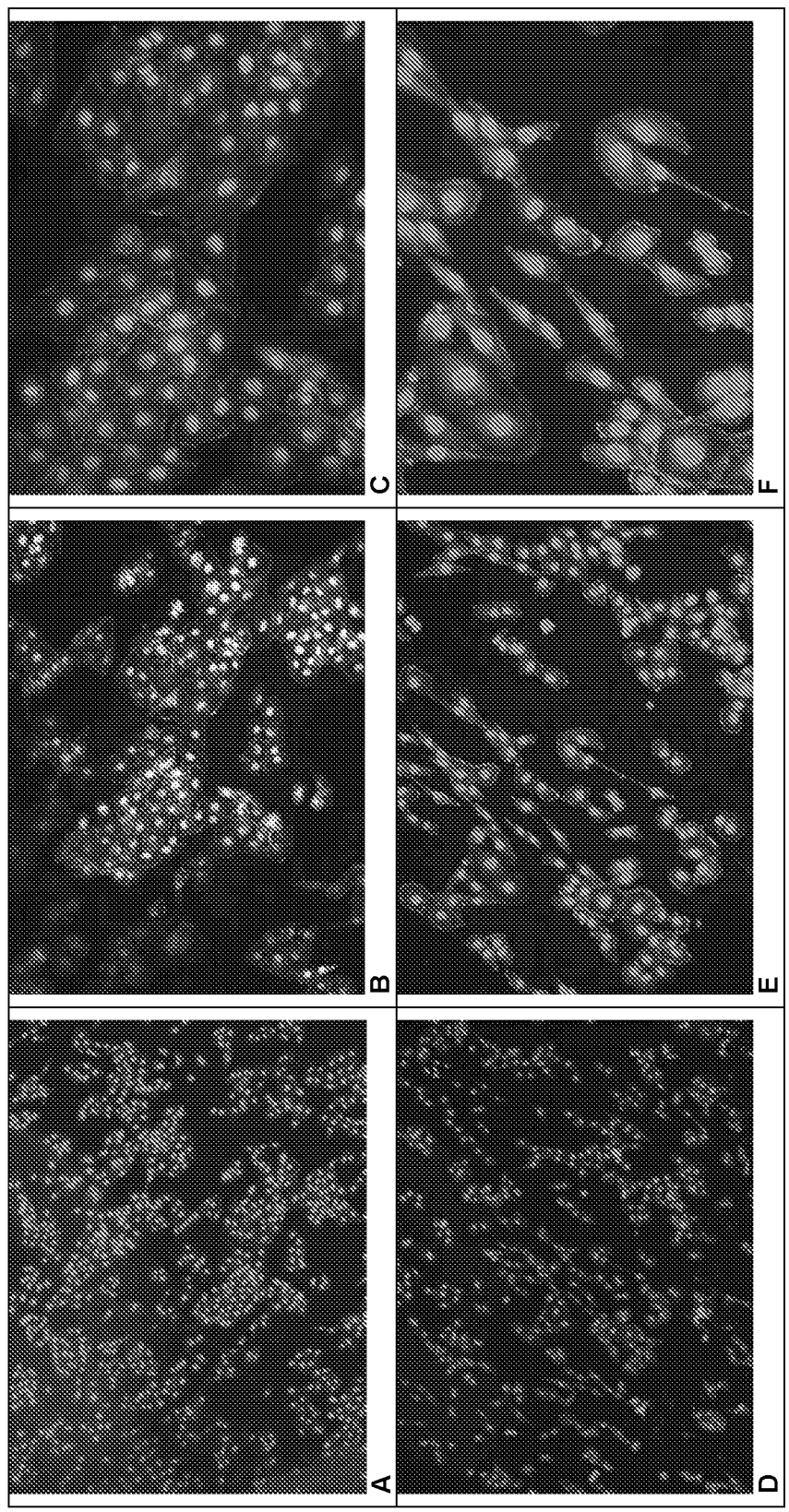
FIGS. 20A-20F show fluorescence images of adhesion of normal human osteoblasts (NHOst cells) on non-coated (FIGS. 20A-20C) and coated (qSiC) surfaces (FIGS. 20D-20F) after 24 hours of culture. The two surfaces appear similar, with an equal number of osteoblasts on the surfaces, indicating the non-cytotoxic nature of the coating.
Figures 21A, 21B, 21C, 21D, 21E, 21F, 21G, 21H, 21I, 21J:
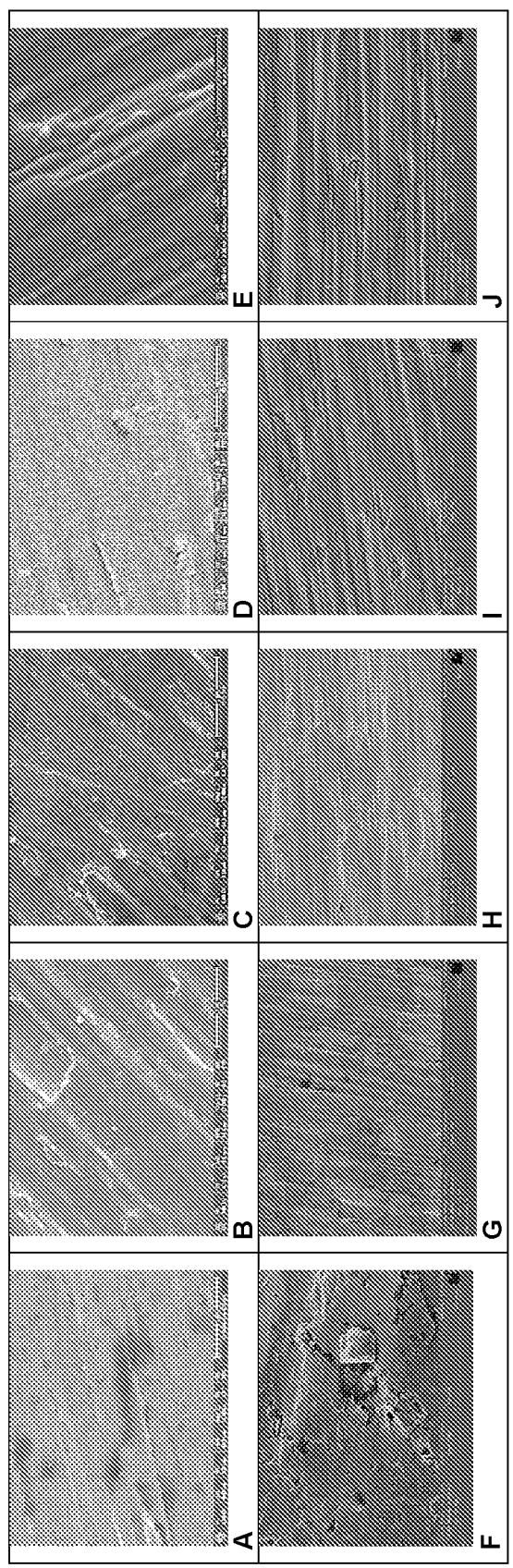
FIGS. 21A-21J show initial SEM images of Ti disks, both coated and non-coated (FIGS. 21A-21E), and the same disks after 30 days cultivation in a culture of *P. gingivalis, S. mutans, S. salivarius*, and *S. sanguinis* (FIGS. 21F-21J).
Figure 22:
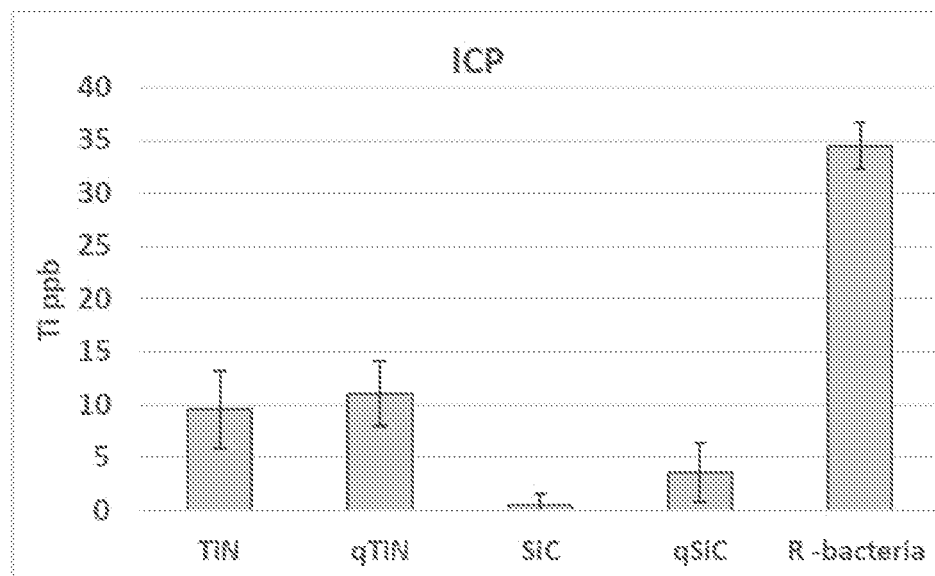
FIG. 22 shows ppb of Ti as determined by ICP-MS for Ti disks that are non-coated (R bacteria on horizontal axis) or coated with TiN, qTiN, SiC, or qSiC. Error bars represent standard deviation.
Figure 23:
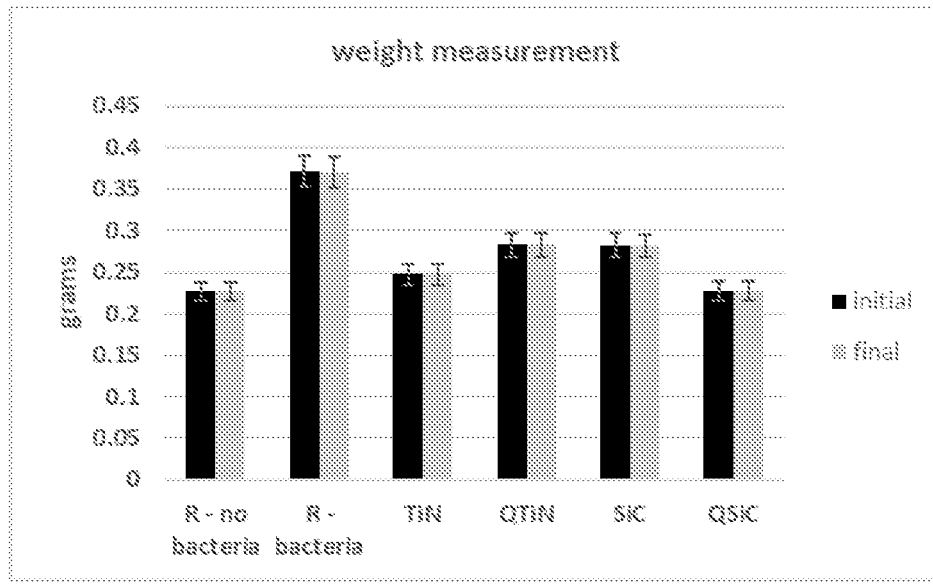
FIG. 23 shows initial and final weights in grams of Ti disks, both coated and non-coated, where final weights are after 30 days of contact with microorganisms. Sample "R—no bacteria" represents a control having no contact with microorganisms, while sample "R—bacteria" represents a non-coated control. Error bars represent standard deviation.

In order to determine whether the qSiC coating impaired cell proliferation, a fluorescence assay was performed. Human osteoblasts (NHOst cells, Lonza, USA) were cultivated for 24 h. Samples that were coated with qSiC showed a cell proliferation similar to the control group (p=0.1923), indicating biocompatibility and/or lack of cytotoxicity (FIG. 19).

The fluorescence images in FIGS. 20A-20F demonstrate cell adhesion and proliferation after 24 h in culture on the surfaces of non-coated control group and the qSiC coated group.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

ASPECTS

The following list of exemplary aspects supports and is supported by the disclosure provided herein.

Aspect 1. A medical apparatus comprising a substrate and a coating comprising a silicon carbide coating, a quaternized silicon carbide coating, a titanium nitride coating, or a quaternized titanium nitride coating.

Aspect 2. The medical apparatus of aspect 1, wherein the substrate comprises a ceramic material, a glass-ceramic material, a zirconia material, or a metal.

Aspect 3. The medical apparatus of aspect 2, wherein the ceramic material, glass-ceramic material, or zirconia is selected from 3Y-TZP zirconia, 12Ce-TZP/$Al_2O_3$ zirconia, alumina ($Al_2O_3$), spinel ($MgAl_2O_4$), lithium disilicate ($Li_2Si_2O_6$), feldspar ($(Na,K)AlSi_3O_8$), leucite ($KAlSi_2O_6$), fluorapatite ($Ca_5(PO_4)_3F$), or a combination thereof.

Aspect 4. The medical apparatus of aspect 2, wherein the glass-ceramic material is fluorapatite.

Aspect 5. The medical apparatus of aspect 2, wherein the metal is selected from gold, a gold alloy, stainless steel, a cobalt-chromium alloy, titanium, a Ti-6Al-4V alloy, a nickel-chromium alloy, an iron-chromium-nickel alloy, platinum, iridium, tantalum, tungsten, or a combination thereof.

Aspect 6. The medical apparatus of any of aspects 1-5, further comprising a metal layer, metal compound layer, or metal oxide layer between the substrate and the silicon carbide or titanium nitride coating.

Aspect 7. The medical apparatus of aspect 6, wherein the metal layer, metal compound layer, or metal oxide layer comprises Ti, TiN, TiC, $TiO_2$, $Ti_3O_5$, $Ti_2O_3$, TiO, $Ti_6Al_4V$, $TiSiC_2$, SiNO, $Al_2O_3$, $HfO_2$, $HfSiO_4$, $Y_2O_3$, $ZrO_2$, $La_2O_3$, SrO, $Ta_2O_5$, $ZrSO_4$, or a combination thereof.

Aspect 8. The medical apparatus of aspect 6 or 7, wherein the metal layer, metal compound layer, or metal oxide layer comprises a passivated layer.

Aspect 9. The medical apparatus of aspect 8, wherein the passivated layer comprises $SiO_2$.

Aspect 10. The medical apparatus of any of aspects 1-9, wherein the medical apparatus comprises a dental prosthesis or a replacement joint.

Aspect 11. The medical apparatus of aspect 10, wherein the dental prosthesis comprises a crown, a post for restoring endodontically treated teeth, a tooth veneer, a partial denture, a palatal obturator, a removable metal framework for dentures, implant-supported bars for denture retention, a removable denture attachment, an orthodontic appliance, or a combination thereof.

Aspect 12. The medical apparatus of aspect 10, wherein the replacement joint comprises a hip joint, a knee joint, a temporomandibular joint, or an elbow joint.

Aspect 13. The medical apparatus of any of aspects 1-12, wherein the quaternized silicon carbide or quaternized titanium nitride comprises a plurality of quaternary nitrogen atoms, wherein the quaternary nitrogen atoms comprise an alkyl group or an alkenyl group.

Aspect 14. The medical apparatus of aspect 13, wherein the quaternary nitrogen atoms comprise an allyl group.

Aspect 15. A coated medical apparatus produced by the method comprising:
(a) forming a vapor of methane and silane; and
(b) applying the vapor to the surface of a medical apparatus to produce that solidifies to a silicon carbide layer on the surface of the coated medical apparatus.

Aspect 16. The coated medical apparatus of aspect 15, wherein the method further comprises:
(c) exposing the medical apparatus containing a silicon carbide layer to a plasma to add nitrogen atoms to the silicon carbide layer;
(d) reacting the nitrogen atoms with an allyl halide to quaternize the nitrogen atoms.

Aspect 17. The coated medical apparatus of aspect 16, wherein the plasma is ammonia.

Aspect 18. The coated medical apparatus of aspect 16 or 17, wherein the allyl halide comprises allyl bromide, allyl chloride, allyl iodide, or a combination thereof.

Aspect 19. The coated medical apparatus of any of aspects 15-18, wherein the SiC layer or quaternized SiC layer is from about 50 μm to about 1000 μm thick.

Aspect 20. A method for improving the antimicrobial properties of a medical apparatus coated with a silicon carbide (SiC) layer, the method comprising reacting the SiC layer with ammonia to incorporate nitrogen atoms into the SiC layer and further comprising reacting the nitrogen atoms with an allyl halide.

Aspect 21. The method of aspect 20, wherein the allyl halide comprises allyl bromide, allyl chloride, allyl iodide, or a combination thereof.

Aspect 22. A coated medical apparatus produced by the method comprising sputter coating a medical apparatus in an inert gas with a TiN target to form a TiN layer.

Aspect 23. The coated medical apparatus of aspect 22, wherein the inert gas comprises argon.

Aspect 24. The coated medical apparatus of any of aspects 22-23, wherein sputter coating is accomplished using a platen bias of about 30 V.

Aspect 25. The coated medical apparatus of any of aspects 22-24, further comprising reacting nitrogen atoms in the TiN layer with an allyl halide to quaternize the nitrogen atoms.

Aspect 26. The coated medical apparatus of aspect 24 wherein the allyl halide comprises allyl bromide, allyl chloride, allyl iodide, or a combination thereof.

Aspect 27. The coated medical apparatus of any of aspects 22-26, wherein the TiN layer is from about 20 nm to about 200 nm thick.

Aspect 28. The coated medical apparatus of any of aspects 22-26, wherein the TiN layer is about 50 nm thick.

Aspect 29. The coated medical apparatus of any of aspects 15-28, wherein the coating comprises antimicrobial properties.

Aspect 30. The coated medical apparatus of aspect 29, wherein the coated medical apparatus reduces microbe-induced corrosion.

Aspect 31. The coated medical apparatus of aspect 29 or 30, wherein the coated medical apparatus is biocompatible.

Aspect 32. A method for improving the antimicrobial properties of a medical apparatus coated with a silicon carbide (SiC) layer, the method comprising reacting the SiC layer with ammonia to incorporate nitrogen atoms into the SiC layer and further comprising reacting the nitrogen atoms with an allyl halide.

Aspect 33. A method for improving the antimicrobial properties of a medical apparatus coated with a titanium nitride (TiN) layer, the method comprising reacting nitrogen atoms in the TiN with an allyl halide.

Aspect 34. The method of aspect 32 or 33, wherein the allyl halide comprises allyl bromide, allyl chloride, allyl iodide, or a combination thereof.

Aspect 35. The method of any of aspects 32-34, wherein the medical apparatus comprises titanium.

Aspect 36. The medical apparatus or coated medical apparatus of any of aspects 1-19 or 22-31, wherein performing the method causes less than 35 ppb titanium to be released from the medical apparatus into a surrounding medium after 30 days of exposure to at least one microbial species.

Aspect 37. The medical apparatus or coated medical apparatus of any of aspects 1-19 or 22-31, wherein less than 15 ppb of titanium is released from the medical apparatus or coated medical apparatus into a surrounding medium after 30 days of exposure to at least one microbial species.

Aspect 38. The medical apparatus or coated medical apparatus of any of aspects 1-19 or 22-31, wherein less than 10 ppb titanium is released from the medical apparatus or coated medical apparatus into a surrounding medium after 30 days of exposure to at least one microbial species.

Aspect 39. The medical apparatus or coated medical apparatus of any of aspects 1-19 or 22-31, wherein less than 5 ppb titanium is released from the medical apparatus or coated medical apparatus into a surrounding medium after 30 days of exposure to at least one microbial species.

Aspect 40. The medical apparatus or coated medical apparatus of any of aspects 1-19 or 22-31, wherein the medical apparatus or coated medical apparatus experiences no net weight change after 30 days of exposure to at least one microbial species.

Aspect 41. The medical apparatus or coated medical apparatus of any of aspects 1-19 or 22-31, wherein the medical apparatus experiences a weight loss of less than about 1% of initial weight after 30 days of exposure to an acidic environment.

Aspect 42. The medical apparatus or coated medical apparatus of aspect 41, wherein the acidic environment comprises a pH of less than about 3.

Aspect 43. The medical apparatus or coated medical apparatus of aspect 41, wherein the acidic environment has a pH of about 2.

Aspect 44. The medical apparatus or coated medical apparatus of any of aspects 1-19 or 22-31, wherein the medical apparatus or coated medical apparatus comprises a surface roughness (Rq) of less than about 55 mm after 30 days of exposure to at least one microbial species.

Aspect 45. The medical apparatus or coated medical apparatus of any of aspects 1-19 or 22-31, wherein the medical apparatus or coated medical apparatus comprises a surface roughness (Rq) of less than about 30 mm after 30 days of exposure to at least one microbial species.

Aspect 46. The medical apparatus or coated medical apparatus of any of aspects 1-19 or 22-31, wherein the medical apparatus or coated medical apparatus comprises a surface roughness (Rq) of less than about 25 mm after 30 days of exposure to at least one microbial species.

Aspect 47. The medical apparatus or coated medical apparatus of any of aspects 1-19 or 22-31, wherein the medical apparatus or coated medical apparatus comprises a surface roughness (Rq) of less than about 20 mm after 30 days of exposure to at least one microbial species.

Aspect 48. The medical apparatus or coated medical apparatus of any of aspects 1-19 or 22-31, wherein surface roughness (Rq) of the medical apparatus or coated medical apparatus increases by less than about 15% after 30 days of exposure to at least one microbial species compared to Rq of the medical apparatus or coated medical apparatus prior to exposure to at least one microbial species.

Aspect 49. The medical apparatus or coated medical apparatus of any of aspects 1-19 or 22-31, wherein surface roughness (Rq) of the medical apparatus or coated medical apparatus increases by less than about 10% after 30 days of exposure to at least one microbial species compared to Rq of the medical apparatus or coated medical apparatus prior to exposure to at least one microbial species.

Aspect 50. The medical apparatus or coated medical apparatus of any of aspects 1-19 or 22-31, wherein the medical apparatus or coated medical apparatus has a water contact angle of greater than about 60°.

Aspect 51. The medical apparatus or coated medical apparatus of any of aspects 1-19 or 22-31, wherein the medical apparatus or coated medical apparatus comprises a carbon content of less than about 5 wt % after five years of service.

Aspect 52. The medical apparatus or coated medical apparatus of any of aspects 1-19 or 22-31, the medical apparatus or coated medical apparatus comprises a biofilm coverage of less than about 20% after 24 hours of exposure to at least one biofilm-forming microbial species.

Aspect 53. A medical apparatus coated with a silicon carbide (SiC) layer or a titanium nitride (TiN) layer, wherein the SiC layer or TiN layer further comprises an alkyl halide derivative or alkenyl halide derivative.

Aspect 54. The medical apparatus of aspect 53, wherein the alkyl halide derivative is a derivative of a C1-C6 alkyl halide.

Aspect 55. The medical apparatus of aspect 53, wherein the alkyl halide derivative is a derivative of a C1-C6 alkenyl halide.

Aspect 56. The medical apparatus of aspect 55, wherein the C1-C6 alkenyl halide is allyl bromide.

Aspect 57. The medical apparatus of any of aspects 48-51, wherein the alkyl halide or alkenyl halide derivative is a quaternary ammonium moiety.

Aspect 58. The medical apparatus of any of aspects 53-57, wherein the medical apparatus comprises a dental prosthesis or a replacement joint.

Aspect 59. The medical apparatus of aspect 58, wherein the dental prosthesis comprises a crown, a post for restoring endodontically treated teeth, a tooth veneer, a partial denture, a palatal obturator, a removable metal framework for dentures, implant-supported bars for denture retention, a removable denture attachment, an orthodontic appliance, or a combination thereof.

Aspect 60. The medical apparatus of aspect 58, wherein the replacement joint comprises a hip joint, a knee joint, a temporomandibular joint, or an elbow joint.

REFERENCES

1. Afonso Camargo, S. E. et al. Anti-Bacterial Properties and Biocompatibility of Novel SiC Coating for Dental Ceramic. J Fund Biomater. 2020, 20, 11, 33. doi: 10.3390/jfb11020033.
2. Ammons M C, et al. Quantitative NMR metabolite profiling of methicillin-resistant and methicillin-susceptible *Staphylococcus aureus* discriminates between biofilm and planktonic phenotypes. J Proteome Res. 2014; 13:2973-2985.
3. An Y H et al. Concise review of mechanisms of bacterial adhesion to biomaterial surfaces. J Biomed Mater Res. 1998; 43:338-348.
4. Auschill T M, et al. The effect of dental restorative materials on dental biofilm. Eur J Oral Sci. 2002; 110: 48-53.
5. Azem, F. A. et al. The corrosion and bioactivity behavior of SiC doped hydroxyapatite for dental applications. Ceramics. Int. 2014, 40, 10, 15881-7.
6. Beech, I. B. et al. Microbially-influenced corrosion: damage to prostheses, delight for bacteria. Int. J. Artif. Organs. 2006, 9, 443-52. doi: 10.1177/039139880602900415.
7. Berbel, L. O. et al. Determinants of corrosion resistance of Ti-6Al-4V alloy dental implants in an In Vitro model of pen-implant inflammation. PLoS One. 2019, 14, 1, 0210530. doi: 10.1371/joumal.pone.0210530. eCollection 2019.
8. Bremer F, et al. In vivo biofilm formation on different dental ceramics. Quintessence Int. 2011; 42:565-574.
9. Bürgers R, et al. In vivo and in vitro biofilm formation on two different titanium implant surfaces. Clin Oral Implants Res. 2010; 21:156-164.
10. Camargo, S. E. A. et al. Novel Coatings to Minimize Bacterial Adhesion and Promote Osteoblast Activity for Titanium Implants. J Funct Biomater. 2020, 11, 42. doi: 10.3390/jfb11020042.
11. Chaturvedi, T. P. An overview of the corrosion aspect of dental implants (titanium and its alloys). Indian J. Dent. Res. 2009,20, 91-8.
12. Chen Z, et al. Demonstration of SiO2/SiC-based protective coating for dental ceramic prostheses. J Am Ceram Soc. 2019:1-9.
13. Cogan, S. F. et al. Plasma-enhanced chemical vapor deposited silicon carbide as an implantable dielectric coating. J. Biomed. Mater. Res. A. 2003, 67, 856-67.
14. Contreras L, et al. Effects of Manufacturing and Finishing Techniques of Feldspathic Ceramics on Surface Topography, Biofilm Formation, and Cell Viability for Human Gingival Fibroblasts. Oper Dent. 2018; 43:593-601.
15. Dağistan S, et al. Differential diagnosis of denture-induced stomatitis, *Candida*, and their variations in patients using complete denture: a clinical and mycological study. Mycoses 2009; 52:266-271.
16. Daguano J K, et al. Bioactivity and cytotoxicity of glass and glass-ceramics based on the $3CaO \cdot P_2O_5$—$SiO_2$—MgO system. J Mater Sci Mater Med. 2013; 24:2171-2180.
17. Daguano J K M B, et al. In vitro biocompatibility of new bioactive lithia-silica glass-ceramics. Mater Sci Eng C Mater Biol Appl. 2019; 94:117-125.
18. Dal Piva A, et al. Monolithic Ceramics: Effect of Finishing Techniques on Surface Properties, Bacterial Adhesion and Cell Viability. Oper Dent. 2018; 43:315-325.
19. Daubert D, et al. Titanium as a modifier of the peri-implant microbiome structure. Clin Implant Dent Relat Res. 2018, 20, 6, 945-953. doi: 10.1111/cid.12676.
20. De la Garza-Ramos, M. A. et al. Electrochemical Behavior of Ti6Al4V Alloy Used in Dental Implants Immersed in *Streptococcus gordonii* and *Fusobacterium nucleatum* Solutions. Materials (Basel). 2020, 21, 13, 4185. doi: 10.3390/ma13184185.
21. de Waal, Y. C. et al. Microbial characteristics of peri-implantitis: a case-control study. J. Periodontol. 2016, 1-13.
22. Di Giulio, M. et al. *Porphyromonas gingivalis* biofilm formation in different titanium surfaces, an in vitro study. Clin. Oral Implants Res. 2016, 27, 918-25.
23. do Nascimento, C. et al. Microbiome of titanium and zirconia dental implants abutments. Dent. Mater. 2016,32, 93-101.
24. Dreyer, H. et al. Epidemiology and risk factors of peri-implantitis: A systematic review. J. Period. Res. 2018, 53, 5, p. 657-681.
25. Egawa, M. et al. In vitro adherence of periodontopathic bacteria to zirconia and titanium surfaces. Dent. Mater. J. 2013, 32, 101-6.
26. Fares, C. et al. Demonstration of a SiC Protective Coating for Titanium Implants. Materials (Basel). 2020, 13, 15, 3321. doi: 10.3390/ma13153321.
27. Flannery A F, et al. PECVD silicon carbide as a chemically resistant material for micromachined transducers. Sensors Actuators A Phys. 1998; 70:48-55.
28. Gil, F. J. et al. The effect of shot blasting and heat treatment on the fatigue behavior of titanium for dental implant applications. Dent. Mater. 2007, 1, 23, 486-91.
29. Gil, F. J. et al. Effect of oral bacteria on the mechanical behavior of titanium dental implants. Int. J. Oral Maxollofac. Impl. 2012, 27, 64-8.
30. Hahnel S, et al. Surface properties and in vitro *Streptococcus mutans* adhesion to self-etching adhesives. J Adhes Den. 2009; 11:263-269.
31. Hahnel S, et al. *Streptococcus mutans* and *Streptococcus sobrinus* biofilm formation and metabolic activity on dental materials. Acta Odontol Scan. 2012; 70:114-121.
32. Hahnel S. et al. Influence of saliva substitute films on initial *Streptococcus mutans* adhesion to enamel and dental substrata. J Dent. 2008; 36:977-83.
33. Harada, R. et al. Corrosion behavior of titanium in response to sulfides produced by *Porphyromonas gingivalis*. Dent. Mater. 2018, 34, 183-91.
34. Harada, R. et al. Influence of sulfide concentration on the corrosion behavior of titanium in a simulated oral environment. Mater. Sci. Eng. C 2016, 62, 268-73.

35. Hsu, S. et al. Novel Coating to Minimize Corrosion of Glass-Ceramics for Dental Applications. Materials 2020, 13, 1215.
36. Ivashchenko V I, et al. Simulations of the mechanical properties of crystalline, nanocrystalline, and amorphous SiC and Si. Phys Rev B 2007; 75:085209.
37. Katsikogianni M, et al. Concise review of mechanisms of bacterial adhesion to biomaterials and of techniques used in estimating bacteria-material interactions. Eur Cells and Materials 2004; 8:37-57.
38. Kidd E A, et al. What constitutes dental caries? Histopathology of carious enamel and dentin related to the action of cariogenic biofilms. J Dent Res. 2004; 83:C35-C38.
39. Kolenbrander P E et al. Oral multispecies biofilm development and the key role of cell-cell distance. Nat Rev Microbiol. 2010; 8:471-480.
40. Li, D. et al. Corrosion and tribo-corrosion behavior of a-SiCx: H, a-SiNx: H and a-SiCxNy: H coatings on SS301 substrate. Surf. Coatings Technol. 2010, 25, 204, 1616-22.
41. Lin, N. et al. In vitro assessments on bacterial adhesion and corrosion performance of TiN coating on Ti6Al4V titanium alloy synthesized by multi-arc ion plating. Appl. Surf. Sci. 2012, 1, 258, 7047-51.
42. Maminskas, J. et al. Novel Yttria-Stabilized Zirconium Oxide and Lithium Disilicate Coatings on Titanium Alloy Substrate for Implant Abutments and Biomedical Application. Materials 2020, 13, 2070.
43. Markowska-Szczupak, A. et al. Are Titania Photocatalysts and Titanium Implants Safe? Review on the Toxicity of Titanium Compounds. Nanomaterials (Basel). 2020, 10, 10, 2065. doi: 10.3390/nano10102065.
44. Meier R, et al. Adhesion of oral streptococci to all-ceramics dental restorative materials in vitro. J Mater Sci Mater Med. 2008; 19:3249-3253.
45. Müller G et al. SiC for sensors and high-temperature electronics. Sensors Actuators A Phys. 1994; 43:259-268.
46. Pabst A M, et al. Influence of CAD/CAM all-ceramic materials on cell viability, migration ability and adenylate kinase release of human gingival fibroblasts and oral keratinocytes. Clinical Oral Investig. 2014; 18:1111-1118.
47. Persson, G. R. et al. Cluster of bacteria associated with peri-implantitis. Clin. Implant Dent. Relat. Res. 2014, 16, 783-93.
48. Piscanec, S. et al. Bioactivity of TiN-coated titanium implants. Acta. Materialia. 2004, 8, 52, 1237-45.
49. Quirynen M, et al. The influence of surface free energy and surface roughness on early plaque formation. An in vivo study in man. J Clin Periodontol. 1990; 17:138-144.
50. Quirynen M, et al. An in vivo study of the influence of the surface roughness of implants on the microbiology of supra- and sub-gingival plaque. J Dent Res. 1993; 72:1304-1309.
51. Roach, M. D. et al. A comparison of the stress corrosion cracking susceptibility of commercially pure titanium grade 4 in Ringer's solution and in distilled water: a fracture mechanics approach. J. Biomed. Mater. Res. B Appl. Biomater. 2014, 102, 73-9.
52. Rodrigues, D. et al. Titanium corrosion mechanisms in the oral environment: a retrieval study. Materials 2013, 6, 5258-74.
53. Rosentritt M et al. In vitro adherence of oral streptococci to zirconia core and veneering glass-ceramics. J Biomed Mater Res B Appl Biomater. 2009; 91:257-263.
54. Safioti, L. M. et al. Increased Levels of Dissolved Titanium Are Associated With Peri-Implantitis—A Cross-Sectional Study. J Periodontol. 2017, 88, 5, 436-442. doi: 10.1902/jop.2016.160524.
55. Sarro P M. Silicon carbide as a new MEMS technology. Sensors Actuators A Phys. 2000; 82:210-218.
56. Souza, J. C. M. et al. Corrosion behaviour of titanium in the presence of *Streptococcus mutans*. *J. Dent.* 2013, 41, 528-34.
57. Sridhar, S. et al. In vitro investigation of the effect of oral bacteria in the surface oxidation of dental implants. Clin. Implant Dent. Relat. Res. 2015, 562-75.
58. Suárez-López, F. D. A. et al. Dental implants-associated release of titanium particles: A systematic review. Clin Oral Implants Res. 2018, 29(11):1085-1100. doi: 10.1111/clr.13372.
59. Sun T et al. Graded Nano Glass-Zirconia Material for Dental Applications-Part II Biocompatibility Evaluation. J Biomed Nanotechnol. 2017; 13:1682-1693.
60. Teughels W et al. Effect of material characteristics and/or surface topography on biofilm development. Clin Oral Impl Res. 2006; 17:68-81.
61. Viitaniemi L et al. Adhesion and Early Colonization of *S. mutans* on Lithium Disilicate Reinforced Glass-Ceramics, Monolithic Zirconia and Dual Cure Resin Cement. Eur J Prosthodont Restor Dent. 2017; 25:228-234.
62. Vo D T et al. Adherence of *Streptococcus mutans* on lithium disilicate porcelain specimens. J Prosthet Dent. 2015; 114:696-701.
63. Wang, R. et al. Antimicrobial property, cytocompatibility and corrosion resistance of Zn-doped ZrO 2/TiO 2 coatings on Ti6Al4V implants. Mater Sci Eng C Mater Biol Appl. 2017, 75, 7-15. doi: 10.1016/j.msec.2017.02.036.
64. Zhang, S. M. et al. Corrosion behavior of pure titanium in the presence of *Actinomyces naeslundii*. J. Mater. Sci. Mater. Med. 2013, 24, 1229-37.
65. Zhu B et al. *Streptococcus sanguinis* biofilm formation & interaction with oral pathogens. Future Microbiol. 2018; 13:915-932.

What is claimed is:

1. A medical apparatus comprising a substrate and a coating comprising quaternized silicon carbide or quaternized titanium nitride, wherein the substrate comprises a ceramic material, a glass-ceramic material, a zirconia material, or a metal.

2. The medical apparatus of claim 1, wherein the metal comprises gold, a gold alloy, stainless steel, a cobalt-chromium alloy, titanium, a Ti-6Al-4V alloy, a nickel-chromium alloy, an iron-chromium-nickel alloy, platinum, iridium, tantalum, tungsten, or any combination thereof.

3. The medical apparatus of claim 1, wherein the medical apparatus comprises a dental prosthesis or a replacement joint.

4. The medical apparatus of claim 3, wherein the dental prosthesis comprises a crown, a post for restoring endodontically treated teeth, a tooth veneer, a partial denture, a palatal obturator, a removable metal framework for dentures, implant-supported bars for denture retention, a removable denture attachment, an orthodontic appliance, or a combination thereof.

5. The medical apparatus of claim 3, wherein the replacement joint comprises a hip joint, a knee joint, a temporomandibular joint, or an elbow joint.

6. The medical apparatus of claim 1, wherein the quaternized silicon carbide or quaternized titanium nitride comprises a plurality of quaternary nitrogen atoms, wherein the quaternary nitrogen atoms comprise an alkyl group or an alkenyl group.

7. The medical apparatus of claim 6, wherein the quaternary nitrogen atoms comprise an allyl group.

8. The medical apparatus of claim 1, wherein the coating has a thickness from about 50 μm to about 1000 μm.

9. A coated medical apparatus produced by the method comprising:
   (a) forming a vapor of methane and silane;
   (b) applying the vapor to a surface of a medical apparatus to produce a silicon carbide layer on the surface of the coated medical apparatus;
   (c) exposing the coated medical apparatus containing a silicon carbide layer to an ammonia plasma to add nitrogen atoms to the silicon carbide layer; and
   (d) reacting the nitrogen atoms with an alkyl halide or alkenyl halide to quaternize the nitrogen atoms.

10. A coated medical apparatus produced by the method comprising sputter coating a medical apparatus in argon with a TiN target to form a TiN layer and reacting nitrogen atoms in the TiN layer with an allyl halide to quaternize the nitrogen atoms.

11. The medical apparatus of claim 1, wherein the medical apparatus comprises titanium and less than 35 ppb of the titanium is released from the medical apparatus into a surrounding medium after 30 days of exposure to at least one microbial species.

12. The medical apparatus of claim 1, wherein the medical apparatus experiences no net weight change after 30 days of exposure to at least one microbial species.

13. The medical apparatus of claim 1, wherein the medical apparatus experiences a weight loss of less than about 1% of initial weight after 30 days of exposure to an acidic environment.

14. The medical apparatus of claim 1, wherein in the medical apparatus comprises a surface roughness (Rq) of less than about 55 mm after 30 days of exposure to at least one microbial species.

15. The medical apparatus of claim 1, wherein surface roughness (Rq) of the medical apparatus increases by less than about 15% after 30 days of exposure to at least one microbial species compared to Rq of the medical apparatus or coated medical apparatus prior to exposure to the at least one microbial species.

16. The medical apparatus of claim 1, wherein the medical apparatus has a water contact angle of greater than about 60°.

17. The medical apparatus of claim 1, wherein the medical apparatus comprises a carbon content of less than about 5 wt % after five years of service.

18. The medical apparatus of claim 1, wherein the medical apparatus comprises a biofilm coverage of less than about 20% after 24 hours of exposure to at least one biofilm-forming microbial species.

* * * * *